(12) United States Patent
Smoorenburg

(10) Patent No.: US 8,694,113 B2
(45) Date of Patent: Apr. 8, 2014

(54) PARAMETRIC FITTING OF A COCHLEAR IMPLANT

(75) Inventor: Guido F. Smoorenburg, Utrecht (NL)

(73) Assignee: Cochlear Limited, Macquarie Park, NSW (AU)

( * ) Notice: Subject to any disclaimer, the term of this patent is extended or adjusted under 35 U.S.C. 154(b) by 759 days.

(21) Appl. No.: 10/518,812

(22) PCT Filed: Jun. 26, 2003

(86) PCT No.: PCT/AU03/00804
§ 371 (c)(1),
(2), (4) Date: Oct. 11, 2005

(87) PCT Pub. No.: WO2004/004412
PCT Pub. Date: Jan. 8, 2004

(65) Prior Publication Data
US 2006/0235332 A1    Oct. 19, 2006

(30) Foreign Application Priority Data
Jun. 26, 2002  (AU) ........................................ PS3182

(51) Int. Cl.
*A61N 1/18* (2006.01)
*H04R 25/00* (2006.01)

(52) U.S. Cl.
USPC .............................................. 607/57; 607/55

(58) Field of Classification Search
USPC ..................................................... 607/55–57
See application file for complete search history.

(56) References Cited

U.S. PATENT DOCUMENTS

| 4,114,627 A | 9/1978 | Lewyn et al. |
| 4,305,396 A | 12/1981 | Wittkampf et al. |
| 4,343,312 A | 8/1982 | Cals et al. |
| 4,373,531 A | 2/1983 | Wittkampf et al. |
| 4,400,590 A | 8/1983 | Michelson |
| 4,532,930 A | 8/1985 | Crosby et al. |
| 4,543,956 A | 10/1985 | Herscovici |

(Continued)

FOREIGN PATENT DOCUMENTS

| EP | 0282336 | 9/1988 |
| EP | 0836363 | 4/1998 |

(Continued)

OTHER PUBLICATIONS

PCT/AU2003/000804 Austrian First Office Action (English Translation).

(Continued)

*Primary Examiner* — Rex R Holmes
(74) *Attorney, Agent, or Firm* — K&L Gates, LLP

(57) ABSTRACT

A method of fitting an auditory stimulation system to a recipient the system having a plurality of channels, and the method including the steps of establishing an initial current level profile representative of a current level setting spanning across at least some of the plurality of channels and adjusting parameters of the initial current level profile in the presence of a stimulation signal. There is further included a programming apparatus adapted to be interfaced with the auditory stimulation system to allow manipulation of threshold (T) and comfort (C) levels of the system. The apparatus includes a graphical display means adapted to display a graphical representation of the current profile of the channel array and means for adjusting a current level setting of the current profile of the array.

34 Claims, 18 Drawing Sheets

(56) References Cited

U.S. PATENT DOCUMENTS

| | | | |
|---|---|---|---|
| 4,895,152 | A | 1/1990 | Callaghan et al. |
| 4,941,179 | A | 7/1990 | Bergenstoff et al. |
| 5,016,280 | A | 5/1991 | Engebretson et al. |
| 5,034,918 | A | 7/1991 | Jeong |
| 5,172,690 | A | 12/1992 | Nappholz et al. |
| 5,271,397 | A | 12/1993 | Seligman et al. |
| 5,277,694 | A | 1/1994 | Leysieffer et al. |
| 5,278,994 | A | 1/1994 | Black et al. |
| 5,565,503 | A | 10/1996 | Garcia et al. |
| 5,626,629 | A * | 5/1997 | Faltys et al. ............... 607/57 |
| 5,674,264 | A | 10/1997 | Carter et al. |
| 5,748,651 | A | 5/1998 | Sheynblat |
| 5,758,651 | A | 6/1998 | Nygard et al. |
| 5,895,416 | A | 4/1999 | Barreras, Sr. et al. |
| 5,963,904 | A | 10/1999 | Lee et al. |
| 6,002,966 | A | 12/1999 | Loeb et al. |
| 6,157,861 | A * | 12/2000 | Faltys et al. ............... 607/57 |
| 6,205,360 | B1 | 3/2001 | Carter et al. |
| 6,289,247 | B1 * | 9/2001 | Faltys et al. ............... 607/57 |
| 6,428,484 | B1 | 8/2002 | Battmer et al. |
| 6,430,402 | B1 | 8/2002 | Agahi-Kesheh |
| 6,463,328 | B1 | 10/2002 | John |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,600,955 | B1 | 7/2003 | Zierhofer |
| 6,697,674 | B2 | 2/2004 | Leysieffer |
| 6,731,767 | B1 | 5/2004 | Blamey et al. |
| 6,751,505 | B1 | 6/2004 | Van Den Honert et al. |
| 6,915,166 | B1 | 7/2005 | Stecker et al. |
| 6,951,166 | B1 | 10/2005 | Sickels |
| 7,043,303 | B1 | 5/2006 | Overstreet |
| 7,076,308 | B1 | 7/2006 | Overstreet et al. |
| 7,082,332 | B2 | 7/2006 | Blamey et al. |
| 7,117,038 | B1 | 10/2006 | Overstreet |
| 7,711,133 | B2 | 5/2010 | Goorevich et al. |
| 2001/0049466 | A1 | 12/2001 | Leysieffer et al. |
| 2002/0026091 | A1 | 2/2002 | Leysieffer |
| 2004/0098063 | A1 | 5/2004 | Goetz |
| 2004/0167586 | A1 | 8/2004 | Overstreet |
| 2005/0015133 | A1 | 1/2005 | Ibrahim et al. |
| 2005/0101878 | A1 | 5/2005 | Daly et al. |
| 2005/0107845 | A1 | 5/2005 | Wakefield et al. |
| 2005/0245991 | A1 | 11/2005 | Faltys et al. |
| 2007/0084995 | A1 | 4/2007 | Newton et al. |
| 2007/0255344 | A1 | 11/2007 | Van Dijk |
| 2008/0319508 | A1 | 12/2008 | Botros et al. |
| 2009/0043359 | A1 | 2/2009 | Smoorenburg |
| 2010/0268302 | A1 | 10/2010 | Botros |

FOREIGN PATENT DOCUMENTS

| | | |
|---|---|---|
| EP | 2222369 | 9/2010 |
| WO | 9210134 | 6/1992 |
| WO | 9324176 | 12/1993 |
| WO | 9414376 | 7/1994 |
| WO | 9501709 | 1/1995 |
| WO | 9612383 | 4/1996 |
| WO | 9709863 | 3/1997 |
| WO | 9748447 | 12/1997 |
| WO | WO 00/052963 | 9/2000 |
| WO | WO 0052963 A1 * | 9/2000 |
| WO | 0076436 | 12/2000 |
| WO | 0113991 | 3/2001 |
| WO | 01/56521 A1 | 8/2001 |
| WO | 02/082982 A1 | 10/2002 |
| WO | 03070322 | 8/2003 |
| WO | 2004/004412 A1 | 1/2004 |
| WO | 2004/021885 | 3/2004 |
| WO | 2004/080532 A1 | 9/2004 |
| WO | 2005/006808 A1 | 1/2005 |
| WO | 2005/122887 | 12/2005 |
| WO | WO-2008031169 | 3/2008 |
| WO | WO-2009076721 | 6/2009 |
| WO | 2009/124035 | 10/2009 |

OTHER PUBLICATIONS

Brown et al. "The Relationship Between EAP and EABR Thresholds and Levels Used to Program the Nucleus 24 Speech Processor: Data from Adults" Ear and Hearing. 2000, Lippincott Williams & Wilkins, U.S.A.

PCT/AU2003/000804 Written Opinion. Mailed Oct. 16, 2003.

PCT/AU2003/000804 International Search Report. Mailed Aug. 26, 2003.

Abbas et al., "Electrically Evoked Compound Action Potentials Recorded from Subjects Who Use the Nucleus CI24M Device," Ann. Otol. Rhinol. Laryngol. Suppl.; Dec. 2000; 185: pp. 6-9.

Abbas et al., "Summary of Results Using the Nucleus CI24M Implant to Record the Electrically Evoked Compound Action Potential," Ear and Hearing, vol. 20(1), Feb. 1999, pp. 45-59.

Australian Examiner's First Report for Patent Application No. 2005254100, dated Dec. 17, 2009.

Austrian First Office Action (English Translation) for Austrian Official file No. 3B A 9165/2003-1, related to PCT/AU2003/000804, dated Mar. 20, 2007.

Baumgarte et al., "A Nonlinear Psychoacoustic Model Applied to the ISO MPEG Layer 3 Coder," Proc. 99th Conv. Aud. Eng. Soc., New York, NY, Oct. 1995, preprint 4087.

Brown et al., "Electrically Evoked Whole-Nerve Action Potentials: Data from Human Cochlear Implant Users," Journal of Acoustical Society of America, vol. 18, No. 3, Sep. 1990, pp. 1385-1391.

Charasse et al., "Automatic Analysis of Auditory Nerve Electrically Evoked Compound Action Potential with an Artificial Neural Network," Artificial Intelligence in Medicine, Mar. 3, 2004, pp. 221-229.

Charasse et al., "Comparison of Two Different Methods to Automatically Classify Auditory Nerve Responses Recorded with NRT System," Acta Acustica United with Acustica, vol. 90, Jan. 22, 2004, pp. 512-519.

Cohen et al., "Spatial spread of neural excitation in cochlear implant recipients: comparison of improved ECAP method and psychophysical forward masking," Hearing Research, 179 (2003), pp. 72-87.

Cohen et al., "Spatial spread of neural excitation: comparison of compound action potential and forward-masking data in cochlear implant recipients," International Journal of Audiology 2004, 43, pp. 346-355.

Delgado et al., "Automated Auditory Brainstem Response Interpretation," IEEE Engineering in Medicine and Biology, Apr./May 1994, pp. 227-237.

Dijk et al., "Development of a Prototype Fully-Automated Intra-Operative ECAP Recording Tool, Using NRT(TM) v3," 2003 Conference on Implantable Auditory Prostheses, 2003, 7 pages total.

Dillier et al., "Measurement of the Electrically Evoked Compound Action Potential via a Neural Response Telemetry System," Annals of Otology, Rhinology & Laryngology, vol. 111, No. 5, May 2002, pp. 407-414.

Edler et al., "ASAC—Analysis/Synthesis Audio Codec for Very Low Bit Rates," Proc. 100th Conv. Aud. Eng. Soc., May 1996, preprint 4179.

European Search Report (Annex), EP 01 95 9971, dated Aug. 2, 2005.

Franck et al., "Estimation of Psychophysical Levels Using the Electrically Evoked Compound Action Potential Measured with the Neural Response Telemetry Capabilities of Cochlear Corporation's CI24M Device," Ear & Hearing, vol. 22, No. 4, Aug. 2001, pp. 289-299.

Franck, "A Model of a Nucleus 24 Cochlear Implant Fitting Protocol Based on the Electrically Evoked Whole Nerve Action Potential," Ear & Hearing, vol. 23, No. 1S, Feb. 2002, pp. 67S-71S.

Hartmann et al., "Evoked Potentials from the Auditory Nerve Following Sinusoidal Electrical Stimulation of the Cochlea: New Possibilities for Preoperative Testing in Cochlear-Implant Candidates?", Acta Otoloaryngol (Stockh) 1994,114, pp. 495-500.

Hughes et al., "Comparison of EAP Thresholds with MAP Levels in the Nucleus 24 Cochlear Implant: Data from Children," Ear and Hearing, vol. 21(2), Apr. 2000, pp. 164-174.

(56) References Cited

OTHER PUBLICATIONS

International Preliminary Examination Report for PCT/AU2003/000804, dated Dec. 20, 2006.
International Preliminary Examination Report for PCT/FR2003/000577, dated May 7, 2004 (English translation).
International Preliminary Examination Report, PCT/AU01/01032, dated Apr. 10, 2002.
International Preliminary Examination Report, PCT/AU02/00500, dated Feb. 12, 2003.
International Preliminary Report on Patentability for PCT/US2005/021207, dated Dec. 20, 2006.
International Search Report for PCT/FR2003/00577, dated Jul. 4, 2003.
International Search Report for PCT/US2005/21207, dated Feb. 8, 2006.
International Search Report for PCT/US2009/038932, dated Jun. 5, 2009.
International Search Report, PCT/AU01/01032, dated Oct. 5, 2001.
International Search Report, PCT/AU02/00500, dated Jun. 26, 2002.
Lai et al., "A Simple Two-Component Model of the Electrically Evoked Compound Action Potential in the Human Cochlea," Audiology & Neuro—Otology, Nov./Dec. 2000; 5: pp. 333-345.
Miller et al., "An Improved Method of Reducing Stimulus Artifact in the Electrically Evoked Whole-Nerve Potential," Ear & Hearing, vol. 21, No. 4, Aug. 2000, pp. 280-290.
Nicolai et al., Performance of Automatic Recognition Algorithms in Nucleus Neural Response Telemetry (NRT(TM)), 2003 Conference on Implantable Auditory Prostheses, 2003, one page total.
Riedmiller et al., "A Direct Adaptive Method for Faster Backpropagation Learning: The RPROP Algorithm," Proceedings of the International IEEE Conference on Neural Networks—1993, vol. 1, Mar. 28-Apr. 1, 1993, pp. 586-591.
Seyle et al., "Speech Perception Using Maps Based on Neural Response Telemetry Measures," Ear & Hearing, vol. 23, No. 1S, Feb. 2002, pp. 72S-79S.
Smoorenburg et al., "Speech Perception in Nucleus CI24M Cochlear Implant Users with Processor Settings Based on Electrically Evoked Compound Action Potential Thresholds," Audiology & Neuro—Otology, Nov./Dec. 2002; 7: pp. 335-347.
Supplementary Partial European Search Report, EP 02 71 7863 dated Oct. 18, 2005.
Thai-Van et al., "Modeling the Relationship Between Psychophysical Perception and Electrically Evoked Compound Action Potential Threshold in Young Cochlear Implant Recipients: Clinical Implications for Implant Fitting," Cinical Neurophysiology 115 (2004), pp. 2811-2824.
Vannier et al., "Objective Detection of Brainstem Auditory Evoked Potentials with a Priori Information from Higher Presentation Levels," Artificial Intelligence in Medicine, Feb. 21, 2002, pp. 283-301.
Written Opinion for PCT/US2009/038932, dated Jun. 5, 2009.
Written Opinion, PCT/US2005/021207 dated Feb. 8, 2006.
International Preliminary Report on Patentability, PCT/US09/38932, mailed Jun. 21, 2010.
Supplementary European Search Report, EP 05 76 2889, mailed May 11, 2010.
International Search Report issued in PCT/AU2008/001865, mailed Mar. 12, 2009 , 3 pages.
Written Opinion for PCT/AU2008/001865, mailed Mar. 12, 2009, 4 Pages.
International Preliminary Report on Patentability issued in PCT/AU2008/001865, issued Jun. 22, 2010, 5 Pages.

\* cited by examiner

PARAMETRIC FITTING OF A COCHLEAR IMPLANT

CROSS-REFERENCE TO RELATED APPLICATIONS

This application is a national stage application of PCT/AU03/00804, filed on Jun. 26, 2003, which claims the priority of Australian Patent Application No. PS 3182, filed on Jun. 26, 2002. The entire disclosure and contents of the above patents and applications are hereby incorporated by reference.

FIELD OF THE INVENTION

The present invention relates to an improved method of clinically fitting a cochlear implant to a recipient to satisfy the recipient's hearing needs.

DESCRIPTION OF THE PRIOR ART

Cochlear implants have been developed to assist people who are profoundly deaf or severely hearing impaired, by enabling them to experience hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally consisted of two parts, an external speech processor unit and an implanted receiver/stimulator unit. The external speech processor unit has been worn on the body of the user and its main purpose has been to detect the external sound using a microphone and convert the detected sound into a coded signal through an appropriate speech processing strategy.

This coded signal is then sent to the receiver/stimulator unit which is implanted in the mastoid bone of the user, via a transcutaneous link. The receiver/stimulator unit then processes this coded signal into a series of stimulation sequences which are then applied directly to the auditory verve via a series of electrodes positioned within the cochlea, proximal to the modiolus of the cochlea.

With improvements in technology it is possible that the external speech processor and implanted stimulator unit may be combined to produce a totally implantable cochlear implant unit that is capable for operating, at least for a portion of time, without the need for any external device. In such a device, a microphone would be implanted within the body of the user, for example in the ear canal or within the stimulator unit, and sounds would be detected and directly processed by a speech processor within the stimulator unit, with the subsequent stimulation signals delivered without the need for any transcutaneous transmission of signals. Such a device would, however, still have the capability to communicate with an external device when necessary, particularly for program upgrades and/or implant interrogation, and if the operating parameters of the device required alteration.

Typically, following the surgical implantation of a cochlear implant; the recipient must have the implant fitted or customised to conform with the specific demands of that recipient. This procedure is often referred to as programming or "mapping" and is the term given to the process of measuring and controlling the amount of electrical current delivered by the cochlea implant to provide comfortable and usable stimulation to the recipient. This process leads to the creation of a program or map that ensures stimulation from the implant provides a recipient with comfortable and useful auditory perception, and is essential in ensuring that the recipient receives maximum benefit from the cochlear implant. As the implant system is designed to present acoustic information, in particular speech, to a recipient in a useable form, the initial aim of the mapping process is to optimise the information provided for a particular recipient.

A fundamental aspect of this procedure is the collection and determination of recipient specific parameters such as threshold levels (known as T levels) and maximum comfort levels (known as C levels) for each stimulation channel. The T and C levels vary from recipient to recipient and from stimulation channel to stimulation channel and are essential in determining how well the recipient hears and understands detected speech or sounds.

Conventionally, the step of determining T and C levels is manually performed by applying stimulation pulses for each electrode channel of the implant and receiving an indication from the implant recipient as to the level and comfort of the resulting sound. The T level is defined as the level at which the recipient first identifies sound sensation, and is the lowest level of stimulation that evokes the sensation of sound for that channel. The T level is often determined by passing the recipient's hearing threshold twice using an ascending method and determining the level at which the recipient experiences sound by observing their response by indicating gestures in the case of adults, or behavioural reactions in the case of children.

The C level sets the maximum allowable stimulation level for each electrode channel and is defined as the maximum stimulation level that feels comfortable to the recipient. In setting and establishing the C levels, it is usual to instruct the recipient to indicate a level which is "as loud as would be comfortable for long periods" whilst slowly increasing the stimulation. The C levels affect how speech sounds to the recipient more than T levels as most of the acoustic speech signal will be mapped onto the top 20% of the T and C level range.

Establishing and setting T and C levels for each electrode channel in a programming process is an important aspect of a fitting session for a cochlear implant. For implants with a large number of electrode channels for stimulation, this process is quite time consuming and rather subjective as it relies heavily on the recipient's subjective impression of the stimulation rather than any specific measurement. This aspect is further complicated in the case of very young children, children with multiple handicapping conditions and/or are developmentally delayed, and pre-lingually or congenitally deaf recipients who are unable to supply an accurate impression of the resultant hearing sensation. In these cases, the fitting of the implant may be non-optimal. In such cases an incorrectly fitted implant will result in the recipient not receiving optimum benefit from the implant and in the cases of children may directly hamper the speech and hearing development of the child.

A number of proposals have been put forward to provide a more objective approach to fitting a cochlear implant to a recipient that reduces the reliance of the process on feedback from the recipient in response to stimulation. However such proposals typically attempt to make an estimate of appropriate T and C levels for each specific electrode channel, and still allow for fine tuning based upon some form of subjective input from the recipient.

U.S. Pat. No. 5,626,629 provides one such approach whereby the T and/or C levels are estimated for each stimulation channel by measuring the stapedius reflex and/or EABR in response to stimulation pulses applied on each of the channels. Such a system enables the mapping process to proceed without relying upon subjective feedback from the recipient, but still requires the objective measurements to be obtained for all of the electrode channels which is both a time consuming and complicated process. Further, when the patient is able to provide subjective feedback, each of the T and C levels for each channel still require manual adjustment, which is a common problem of the prior art.

U.S. Pat. No. 6,157,861 also provides a system for obtaining objective measurements of the T and/or C levels without relying on subjective feedback from the recipient. In this approach, the stapedius reflex is detected for stimulaiion applied on each channel in accordance with a dedicated stapedius reflex sensor system. As was the case in the above mentioned patent, this approach also requires that the stapedius reflex be measured for each specific electrode channel which is both a time consuming and delicate process.

The present invention is directed to a process of programming the operation of a cochlear implant that address the problems described herein.

In order to improve the programming process and decrease the time taken to develop a useful map for a recipient, there is a need to obtain and manipulate the T and C levels more effectively than has previously been the case. In the past, T and C levels have been obtained and manipulated on a one-by-one basis and not globally, taking into consideration the interaction between channels. This has resulted in there being a number of degrees of freedom and a great degree of variability and uncertainty in the manipulation of T and C levels. The present invention aims to reduce the variability and uncertainty associated with setting the T and C levels for a recipient and to concentrate on manipulating these levels parametrically, based upon objective measures, statistical analysis of recipient maps and from other such observations or theoretical considerations.

The present invention preferably provides a method for fitting a speech processor and implantable cochlear stimulator to a particular recipient in a quicker and more effective manner than has historically been the case.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

In accordance with one aspect of the invention, there is provided a method of fitting an auditory stimulation system having a plurality of channels to a recipient, the method comprising the steps of:

establishing an initial current level profile representative of a current level setting spanning across at least some of the plurality of channels; and adjusting parameters of the initial current level profile in the presence of an stimulation signal.

In a further embodiment of this aspect, the method can further comprise a step of:

determining the desired parameters representative of an optimum current level profile corresponding to a recipient's threshold and/or maximum comfort current level profile.

According to a second aspect of the invention, there is provided a programming apparatus adapted to be interfaced with an auditory stimulation system having a plurality of channels to allow manipulation of the threshold (T) and comfort (C) levels of the system, the programming apparatus comprising:

a graphical display means adapted to display a graphical representation of the current profile of the channel array; and means for adjusting a current level setting of the current profile of the array.

In a preferred embodiment, the auditory stimulation system comprises a cochlear implant system. The cochlear implant system preferably utilises an electrode array to deliver electrical stimulations to the cochlear of a recipient. In one embodiment, the array comprises 22 intracochlear electrodes and at least one extracochlear electrode.

By manipulating the parameters of a current level profile spanning preferably all electrode channels of the electrode array, there is no need to adjust threshold and comfort level currents for each individual electrode channel in the array of an implant following implantation in the recipient. Instead, manipulation is preferably applied to the entire channel profile resulting in a greatly reduced amount of psychophysical measurements required and a programming/fitting procedure that is more recipient friendly, more time efficient and more cost effective.

Preferably, the step of establishing an initial current level profile includes a step of obtaining measurements of the evoked compound action potential (ECAP) thresholds for each or a number of the electrode channels and establishing a current level profile based upon these measurements. In another embodiment, the initial current level profile is preferably established from measurements of the ECAP thresholds for at least one electrode channel of the auditory stimulation system, with the full profile being interpolated from such measurements.

In another embodiment, the step of establishing an initial current level profile includes the step of performing a statistical analysis of recipient mapping data over a number of recipients and using this analysis to form an initial current level profile for a particular recipient.

In yet another embodiment, the step of establishing an initial current level profile includes the step of performing a number of psychophysical and/or electrophysiological measurements of the recipient in combination with statistical analysis of recipient mapping data over a number of recipients to determine a suitable initial current level profile for a particular recipient.

The initially determined suitable current level profile is preferably represented on the graphical display means of the programming apparatus to allow ready determination by a clinician of the current profile of the array.

The step of adjusting the overall parameters of the initial current level profile preferably includes adding/subtracting a fixed or derived amount of current level from each individual electrode channel in the profile. This parameter adjustment is referred to as a "shift" manipulation, and has the effect of moving the profile up or down in a vertical direction on a graph plotting current level against electrode channel number.

By "shifting" the profile "up", either a fixed amount of current is added to the current level of each individual electrode channel in the profile (linear shift), or an individually derived current level is added to each electrode channel (nonlinear shift), thereby increasing the amount of current delivered by the electrode channels when operated with that particular profile.

By "shifting" the profile "down", either a fixed amount of current is subtracted from the current level of each individual electrode channel in the profile (linear shift), or an individually derived current level is subtracted from each electrode channel (non-linear shift), thereby decreasing the amount of current delivered by the electrode channels when operated with that particular profile.

The overall parameters of the initial current profile can also be adjusted by adding an electrode channel specific derived amount of current level to a subset of electrode channels in the profile and subtracting an electrode channel specific derived amount of current level from the remaining electrode channels. This parameter adjustment is preferably referred to as a "tilt" manipulation, and has the effect of tilting the profile clockwise or anti-clockwise on a graph plotting current level against electrode channel. In a preferred embodiment, the "tilt" manipulation may be performed by using at least one electrode channel, for example electrode channel 12 of said plurality of electrode channels, as a pivot point and for each electrode channel 1-11 the individual current levels of each electrode channel is decreased by a varying percentage of a fixed amount of current, and for each electrode channel 13-22, the current level for each electrode is increased by a varying percentage of a fixed amount of current, or vice versa. In this regard and where the electrode array is adapted to be positioned within the cochlea, the electrodes positioned in the apical region may have their current levels increased and those within the basal region may have their current levels decreased, or vice versa. The amount of current level to be added/subtracted from the electrode channel can be a function solely depending on the distance of the electrode channel in question to the pivot point (linear tilt) or can have a more complex dependency, e.g. depend from a separate "tilt profile" in addition (non-linear tilt).

The overall parameters of the initial current level profile can also be adjusted by adding/subtracting a derived amount of current level from each individual electrode channel in the profile in such a way as to bend the current level profile. This can be interpreted as a profile manipulation using 2 pivot points, which might be allocated but are not limited to the most basal and most apical electrode channel. These pivot points might even be situated outside the actual range of electrode channels available. This parameter adjustment can be referred to as a "curvature" manipulation and has the effect of causing the profile to curve or change shape on a graph plotting current level against electrode channel. The "curvature" can be achieved in a linear and non-linear manner, as described above. The derived values used for the non-linear manipulations can stem from statistical analysis, such as factor analysis of available clinical data. They can be influenced by several factors, such as the actual starting level, whether it is a T or a C level, the implant and electrode type used or the coding strategy applied. Other sources of influence and any combination of factors can be used to calculate the derived data.

Other parameter manipulations suitable to adjusting the current level profile are also included within the scope of the present invention.

In a preferred embodiment, the step of adjusting the overall parameters of the initial current level profile can include any one or combination of a "shift" manipulation, a "tilt" manipulation and/or a "curvature" manipulation.

Adjustment of the profile is preferably performed through a clinician interface that allows the current profile of the electrode array to be adjusted in the manner described herein. In one embodiment, a software package can be run on a computer, with the software package offering input means that allows the clinician to readily adjust the current profile of the array. The input means can comprise one or more of a mouse, joystick, roller ball, keyboard, or keypad, that allows the clinician to adjust the settings within the software package.

In a preferred embodiment, the overall parameters of the initial current level profile are adjusted in the presence of a broad band signal, preferably a live speech signal. The broadband signal alternatively may be an artificial signal or a recorded signal. In such a case, the implant delivers stimulation representative of the signal, in accordance with the current level profile. By adjusting the parameters of the current level profile the stimulation delivered by the implant varies, allowing the stimulation signal to be optimised in terms of recipient threshold and maximum current levels.

The method and apparatus according to the present invention present a number of potential advantages over existing techniques. In particular, it is envisaged that fewer psychophysical measurements will be needed to prepare a map for a particular recipient and the channels will be manipulated globally rather than individually. The ability to use live sounds is also potentially more interesting for small children than arbitrary stimuli used to date.

BRIEF DESCRIPTION OF THE DRAWINGS

Embodiments of the invention will now be described, by way of example only, with reference to the accompanying drawings, in which.

PREFERRED MODE OF CARRYING OUT THE INVENTION

The following description is directed to a cochlear implant system having an electrode array, in particular an array having twenty-two intracochlear electrodes. It will be appreciated that the invention has potential applicability to any auditory stimulation system utilising an electrode array and in particular to electrode arrays comprising less or more electrodes than that described herein.

Throughout the specification a channel is considered to be a pair of electrodes that provide a path for current to flow. One electrode is called the active electrode and the other is called the reference electrode. Pulses of current flow from the reference to the active electrode and back again to stimulate nearby nerves. Our implant provides up to 22 channels.

In order to better understand the present invention, it is appropriate to firstly consider one method of programming a cochlear implant and creating a map which enables the speech processor to output data in a form which can be decoded by the receiver/stimulator.

As a map is a complete set of instructions for the speech processor which includes the minimum and maximum stimulation levels for each stimulation channel, conventional programming methods have required the clinician creating the map for the recipient of the implant, to measure T and C levels for each channel, for the stimulation mode and speech processing strategy chosen for the recipient. This process requires an experienced clinician/audiologist to present a stimulus, usually a fixed phase biphasic pulse at a fixed rate and duration, to each channel of the recipient's implanted electrode array. The clinician/audiologist then asks the subject to estimate the lowest level at which that stimulus can be detected (T level) and the level judged by the recipient as being the upper limit of comfort (C level). This process is repeated for all of the channels, for example, all 22 electrode channels in a current Nucleus® model device as manufactured by the present applicant, until a map is created which includes T and C levels for each channel that delivers stimulation pulses. It has been found that initial estimates of the T and C levels as determined by the clinician/audiologist working in conjunction with the recipient (where possible) using the conventional method are variable and may take months to stabilise. As such, it is easy to appreciate that the conventional programming method is a laborious task requiring much experience and expertise by the clinician and relying on good feedback from the recipient to create the most optimal map.

Figure 1:
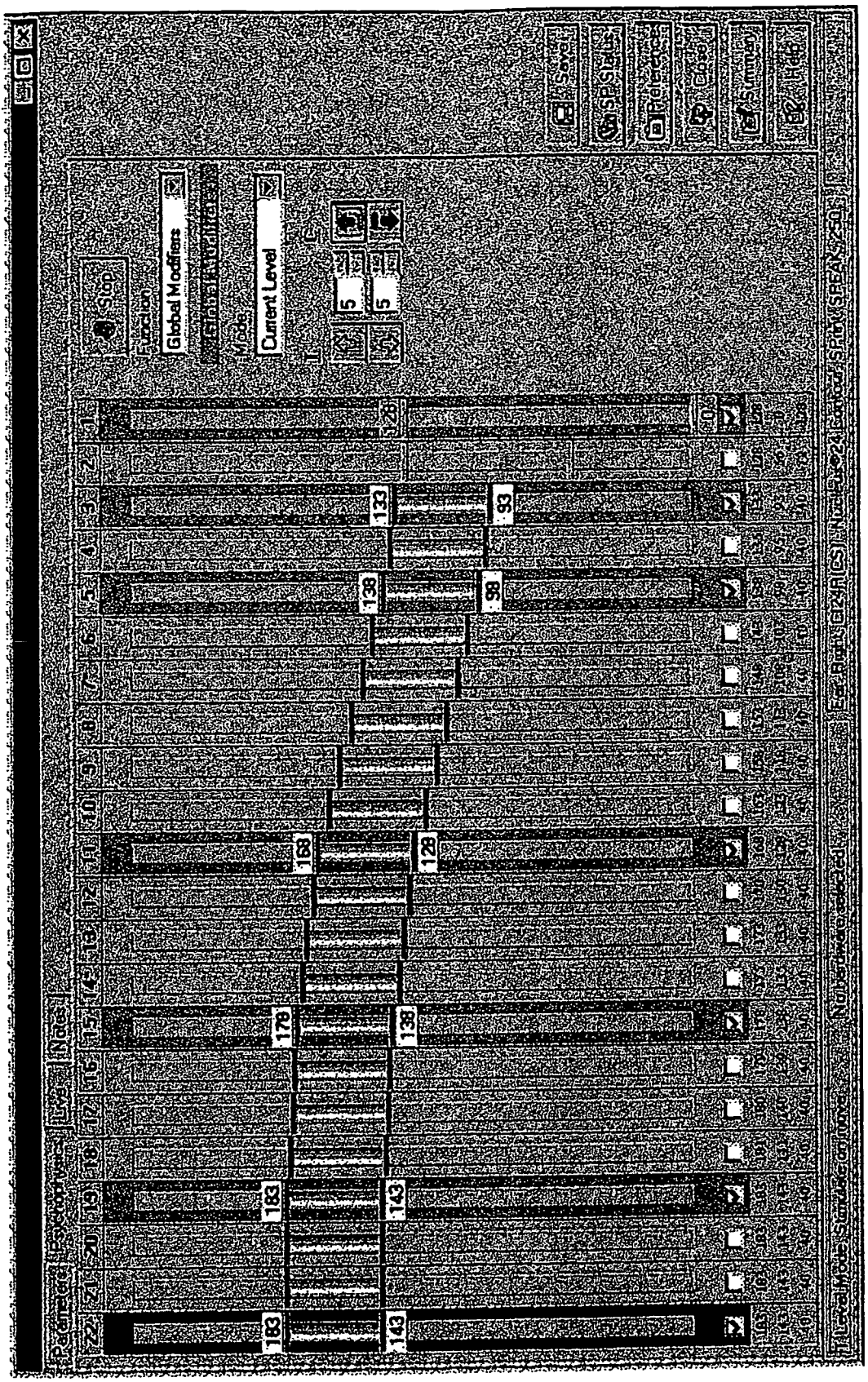
FIG. 1 is a graphical example of a typical recipient map generated by conventional mapping techniques.

FIG. 1 shows the T and C levels for a typical recipient map which may be generated by a clinician during such a mapping session. These levels have been generated using a software package developed by the present applicant to assist the clinician by providing an interface that is easy for the clinician to manipulate and visualise. The horizontal sections numbered 1-22 (along the top) indicate the channel number along the intracochlear array of the implant, and the vertical axis represents current level for each electrode channel in the array. This software package is run on a computer that outputs signals set by the software package through an interface. The interface is adapted to connect to the speech processor and allow transmission of signals from the computer to the processing control system of the speech processor which in turn outputs stimulation signals via the transcutaneous radio frequency (RF) link to the implanted receiver/stimulator unit of the system.

As is shown in this particular example, the upper vertical limit for each channel is the maximum comfort level (C level) which represents for that particular channel, the maximum amount of current which can be delivered to deliver a sensation to the recipient at a loudness level which is just tolerable to that recipient. The lower vertical limit for each channel is the threshold level (T level) which represents the amount of current which can be delivered by that channel to produce a sensation that is just audible to the recipient. In this particular example, the T and C levels for a number of channels are specifically shown, for example the T and C levels for electrode channel 11 are 128 and 168 respectively, and in use all sounds detected are mapped between these 2 levels to produce the equivalent sound sensation to the recipient.

In the software package as shown in FIG. 1, the T and C levels can be altered up or down by the clinician using appropriate controls on the computer so leading to altered signals being sent to the speech processor which in turn adjusts the stimulation signals output by the electrode array. This alteration can be made with feedback from the recipient indicating whether the sensation is either too loud or just audible.

Whilst the conventional mapping techniques are time consuming and arduous for both the clinician and the recipient, there has to date been no reliable alternative implemented on a wide scale. However, with an increased understanding of the response of nerves to electrical stimulation, there has been research into how this increased understanding can assist in understanding the parameters associated with delivering electrical stimulation, and this has suggested possible new ways to improve the conventional mapping process.

For a number of years it has been possible to record the electrically evoked auditory brain stem response (EABR) in cochlear implant recipients and a number of studies have been conducted which have attempted to correlate EABR thresholds to mapped threshold and/or comfort levels. Such EABR measurements have required the use of surface recording electrodes and the complications and lengthy nature of this measuring process have hindered this technique from becoming routinely adopted. Still further, the recipient being assessed has often had to be asleep or heavily sedated to avoid contaminated measurements from being recorded by the recording electrodes.

It is only more recently that a simple and more direct way to assess auditory nerve function in cochlear implants has been possible, by measuring the electrically evoked compound action potential (ECAP). This potential reflects the synchronised response of peripheral auditory nerves delivered by an intracochlear electrode, and the response typically resembles a waveform having an initial negative peak followed by a positive peak. Initially, such ECAP measurements could only be obtained intraoperatively through the use of a temporary intracochlear electrode array, or with cochlear implant recipients having a device with a percutaneous plug. In such cases, the ability to perform such measurements was only done experimentally, and as special instances had to be set up to allow such measurements to be taken, it was not possible to obtain such results for everyday use.

Recent developments undertaken by the present applicant have allowed for a quick and non-invasive method for recording the ECAP of the peripheral auditory nerves in situ, without the need for dedicated devices or plugs. Such a method has been designed into the conventional cochlear implant system to provide an additional feature of the system which can be utilised to take such measurements. The applicant's Nucleus® 24 model cochlear implants were the first implant system with such capabilities, and only now are the benefits of such a feature becoming fully realised.

The feature for recording the ECAPs in the Nucleus® 24 model device is known as Neural Response Telemetry (NRT) and whilst this application focuses on the NRT feature, it should be appreciated that this invention will be also applicable to other such methods of recording ECAPs, and hence should not be limited to use with the specific NRT feature.

In the mentioned feature, the bi-directional telemetry system that is present in the cochlear implant is used to measure the ECAP of the recipient's auditory nerve. Dedicated ECAP measurement software communicates with the implanted receiver/stimulator unit via the speech processor and RF link and biphasic current pulses are delivered to a single intracochlear electrode of the array. The resulting ECAP is measured from a neighbouring electrode, amplified, encoded and sent back to the speech processor via the RF link. The data is then analysed using the speech processor and the dedicated ECAP measurement software, with the software then presenting the results in a manner easily interpreted by a clinician or implant specialist. As mentioned previously, in such a system the ECAP measurement can be taken without the need of any extra equipment, and therefore has considerable advantages over other evoked potential measures, such as the electrically evoked auditory brainstem response (EABR).

U.S. Pat. No. 5,758,651 describes one system and apparatus for recovering ECAP data from a cochlear implant. This system measures the neural response to the electrical stimulation by using the stimulus array to not only apply the stimulation but to also detect and receive the response. In this system the array used to stimulate and collect information is a standard intra-cochlear and/or extra-cochlear electrode array. Following the delivery of a stimulation pulse via chosen stimulus electrodes, all electrodes of the array are open circuited for a period of time prior to measurement of the induced neural response. The purpose of open circuiting all electrodes prior to measurement is to reduce the detected stimulus artefact measured with the ECAP nerve response.

Whilst the above system has proven useful in capturing and investigating evoked neural response in the cochlea, there are still a number of limitations intrinsic with this system, in particular in resolving the neural response from the stimulus artefact. This process has presented considerable difficulties, including problems such as the fact that the signals that are to be measured are extremely low level signals (down to the order of 10 μV).

In cochlear implant applications in particular, a stimulus pulse is delivered with an amplitude typically in the range of 1V to 10V, which is orders of magnitude greater than the response that is to be measured resulting from this stimulation. Providing for a system that is firstly able to deliver a stimulus of sufficient amplitude and also to detect the elicited response of the nerves to that particular stimulation has therefore been problematic. Due to the nature of the neural response, the sensing system must be ready to record this response within a short delay (preferably less than 50 μs) after the trailing edge of the stimulus. In order to properly resolve the very small neural signal a large amplifier gain is required (typically of about 60 dB to 80 dB), however the neural signal is superimposed on a much larger artefact which distorts the actual measured signal considerably.

In order to overcome the above mentioned problems, the system as described in International Patent Application PCT/AU02/00500 was developed which delivers, subsequent to the first stimulus, a compensatory stimulus in order to counteract a residue charge distribution caused by the first stimulus. In this system, the artefacts associated with the stimulus could be addressed at the time of measuring the ECAPs, without the need for post measurement processing, thereby providing a more exact and useable measurement. This application also describes a method of optimising the parameters of the compensatory stimulus to take into account differences in the artefacts present, as may be the case from electrode to electrode or from recipient to recipient.

With improved methods of obtaining such measurements, there has been an interest in investigating ways to use this information in a clinical setting, rather than using the information merely to check that the electrodes are delivering stimulation. A number of initial studies have been undertaken to investigate potential clinical applications of such measurements, with a focus of such measurements being on determining whether the ECAP response can be used to aid in the programming of the cochlear implant speech processor. It is considered that such an application would be beneficial to clinicians and audiologists who work with very young children, where programming the speech processor presents significant challenges.

One such investigation was reported in Brown C J, Hughes M L, Luk B, Abbas P J, Wolaver A, Gervais J (2000) "*The Relationship Between EAP and EABR Thresholds and Levels Used to Program the Nucleus* 24 *Speech Processor: Data from Adults*" Ear & Hearing, 21, 151-163. In this investigation, ECAP thresholds were correlated with conventionally mapped T and C levels and it was shown that the correlation was not sufficiently strong to suggest that ECAP measurements could be directly used without some level of behavioural information.

This investigation suggested that whilst ECAP thresholds alone may not be strong predictors of either T or C levels, a combination of these results with a small amount of behavioural information may allow clinicians working with individuals with limited attention and/or response capabilities to be fitted with a cochlear implant with reasonable accuracy.

This finding was also consistent with a finding reported in Hughes M L, Brown C J, Abbas P J, Wolaver A A, Gervais JP (2000) "*Comparison of EAP Thresholds with MAP Levels in the Nucleus* 24 *Cochlear Implant: Data from Children*" Ear & Hearing, 21, 164-174. In this investigation, ECAP thresholds were shown to fall between T and C levels for 18 out of 20 subjects tested. However, there existed a level of variability across recipients sufficient to make map threshold or comfort level predictions based solely on the objective ECAP measures to have a significant error in most cases. Therefore, the ECAP thresholds could provide an indication of "safe" levels of stimulation.

Figure 2:
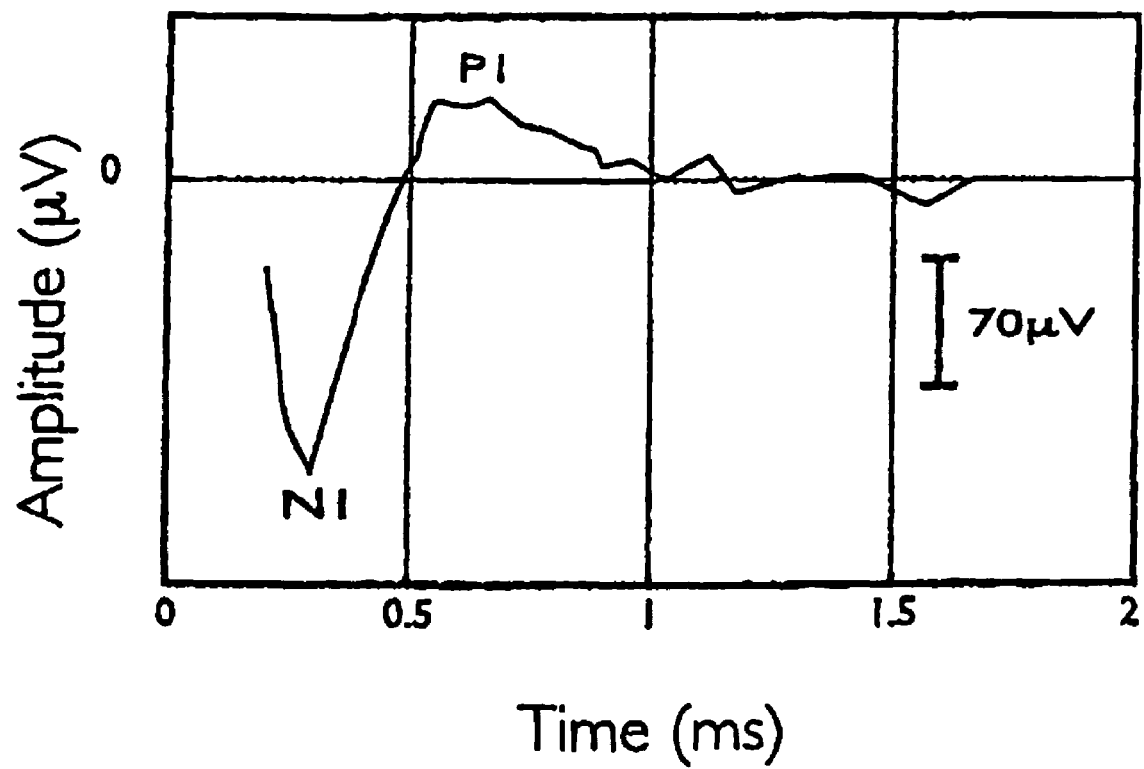
FIG. 2 is a graphical representation of a typical ECAP waveform showing negative (N1) and positive (P1) peaks.

In order to understand this further, a typical ECAP waveform is shown in FIG. 2, with the ECAP waveform consisting of an initial negative peak (labelled N1) followed by a positive peak (labelled P1). Using a recipient's Nucleus® 24 model implant, the ECAP measurement can be taken without the need for any extra equipment, as a neighbouring electrode to that which delivers the stimulation can be used to measure the ECAP, whereby the implant amplifies, encodes, and transmits the signal back to an external unit which then analyses the data with dedicated software, to enable the data to be easily interpreted by the clinician.

Figure 3:
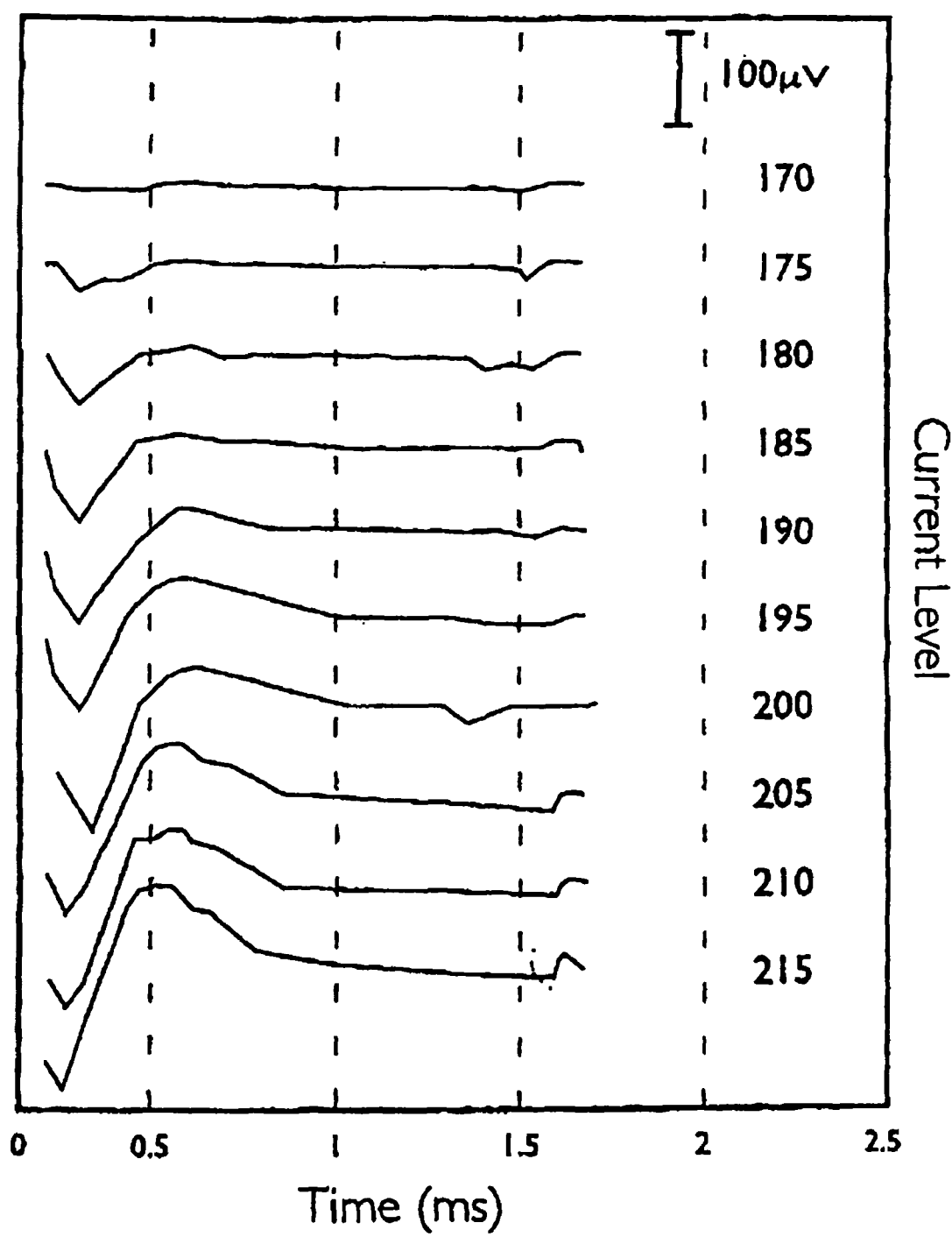
FIG. 3 is a graphical representation of the changes in ECAP as a function of the stimulus current level.
Figure 4:
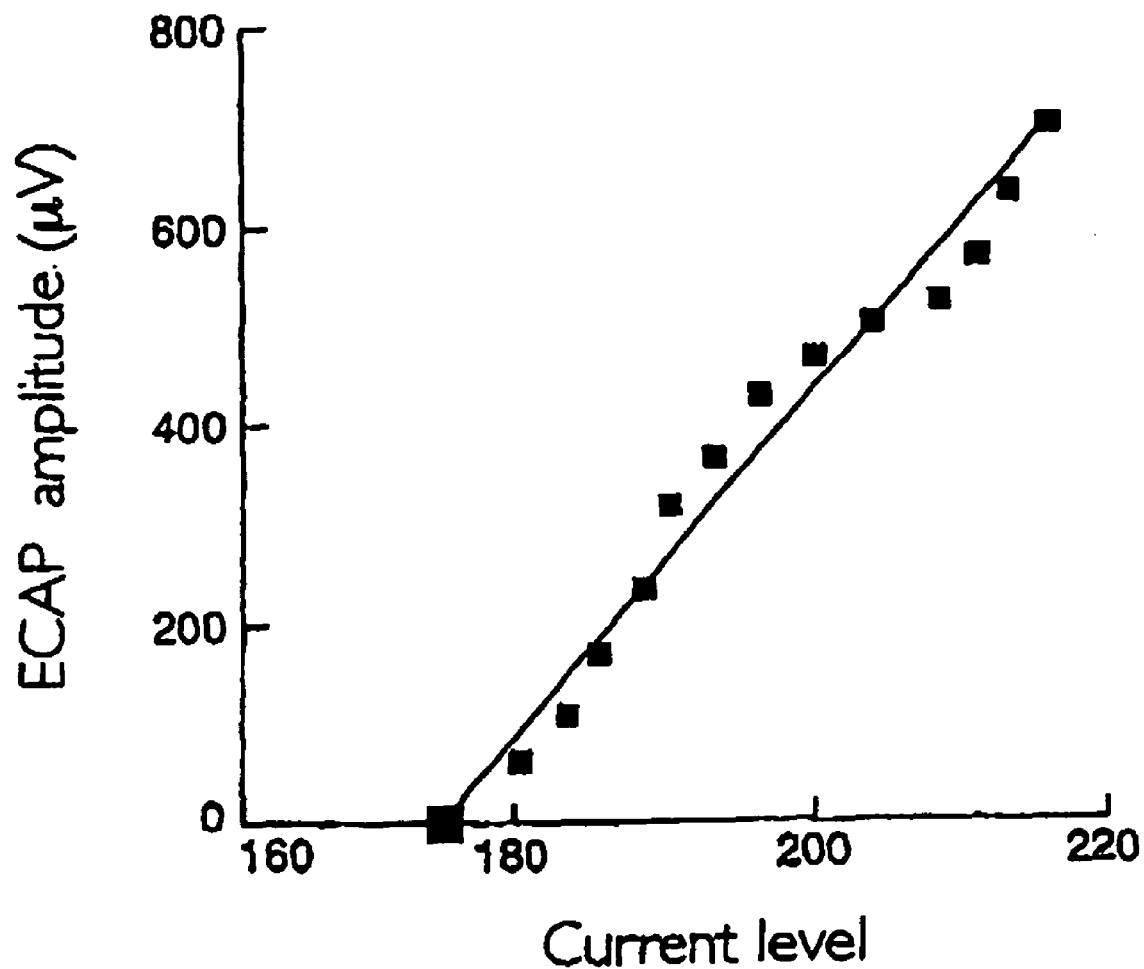
FIG. 4 shows the ECAP growth function.

The N1 and P1 amplitude of the ECAP waveform vary with stimulating current as can be seen in FIG. 3, with the amplitudes increasing with increases in stimulating current level. It is the amplitude growth function that can be used to estimate the ECAP threshold, and to quantify how the response changes with stimulus intensity. This is obtained via dedicated software that uses the ECAP amplitude, which is the difference (in μV) between the N1 and P1 amplitudes, which is evident in the graph in FIG. 2. The ECAP threshold may be estimated visually by reviewing the amplitude growth series and selecting the electrical stimulation level which produces the smallest repeatable N1 and P1 peaks in the waveform, or software can be used to extrapolate the ECAP threshold from the amplitude growth function. As is shown in FIG. 4, the amplitude growth function is a plot of the ECAP amplitudes as a function of stimulus current levels and it has been found that a linear regression line can be fitted to the data to extrapolate the ECAP threshold and to define the slope of the function.

Figure 5:
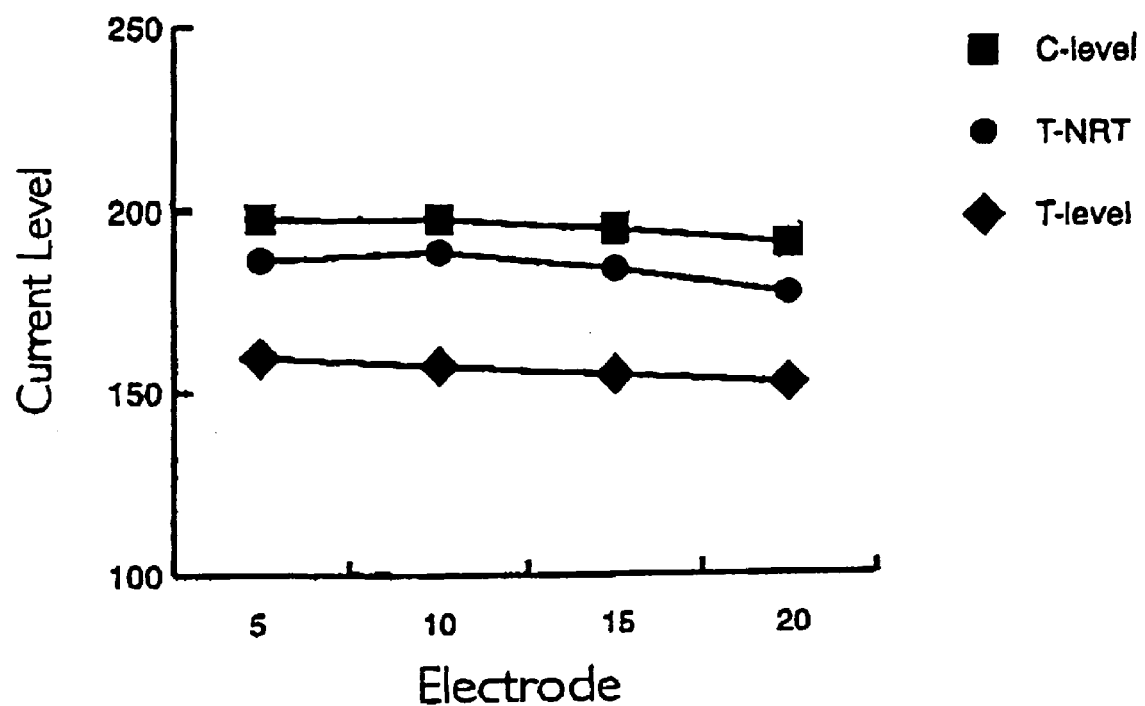
FIG. 5 shows the relationship between the average ECAP thresholds and the behavioural T and C levels for a group of 82 recipients using the Nucleus® 24 implant.

As mentioned above, the clinical value of the ECAP thresholds has been investigated, and it has been shown that there are some important relationships between the current levels of the ECAP thresholds and the behavioural T and C levels established by a clinician during a mapping procedure. The main relationships are that the ECAP thresholds correlate with the behavioural T and C levels, however the ECAP thresholds are not equal to the T or C levels but typically lie between the T and C levels, with the ECAP thresholds being typically audible to the recipient. This aspect is shown in FIG. 5, where there is shown the average ECAP thresholds (T-NRT) and the behavioural T and C levels for a group of 82 recipients using the Nucleus® 24 model implant.

Figure 6:
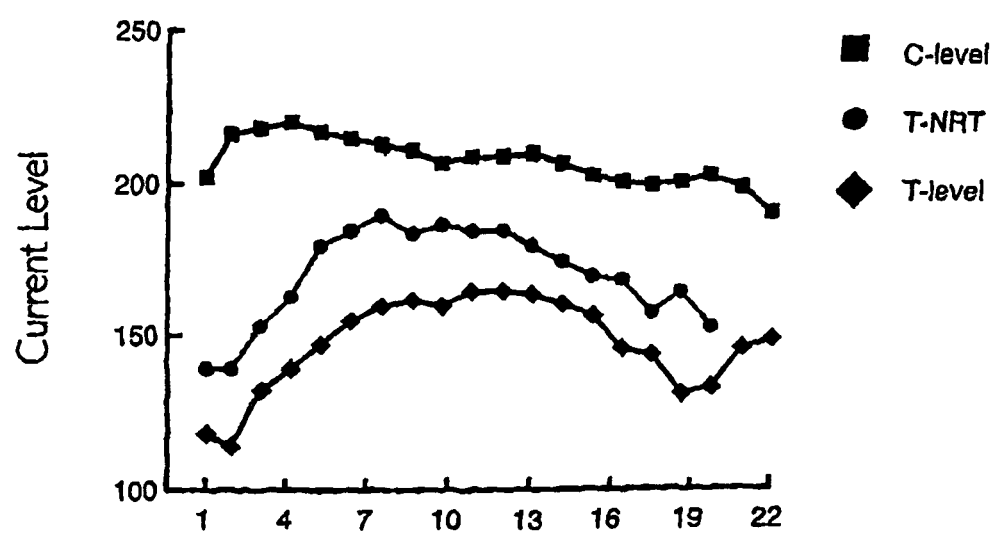
FIG. 6 shows the relationship between the ECAP thresholds and the behavioural T and C levels from a recipient implanted with a Nucleus® 24 Contour™ implant.

A further finding has been the fact that the profile of the ECAP threshold levels as a function of electrode number resembles the profiles of the T levels and to a lesser extent the C levels. This is shown in FIG. 6, where the ECAP threshold profile (T-NRT) and the behavioural T and C levels are shown from a recipient implanted with a Nucleus® 24 model implant and Contour™ model array, which is manufactured by the present applicant.

With this understanding of how objective measurements can be taken which show the response of the peripheral auditory nerves to electrical stimulation delivered by the cochlear implant, there is a need to attempt to utilise these developments to make the fitting/programming session(s) for a cochlear implant more user friendly and clinically efficient.

Figure 7:
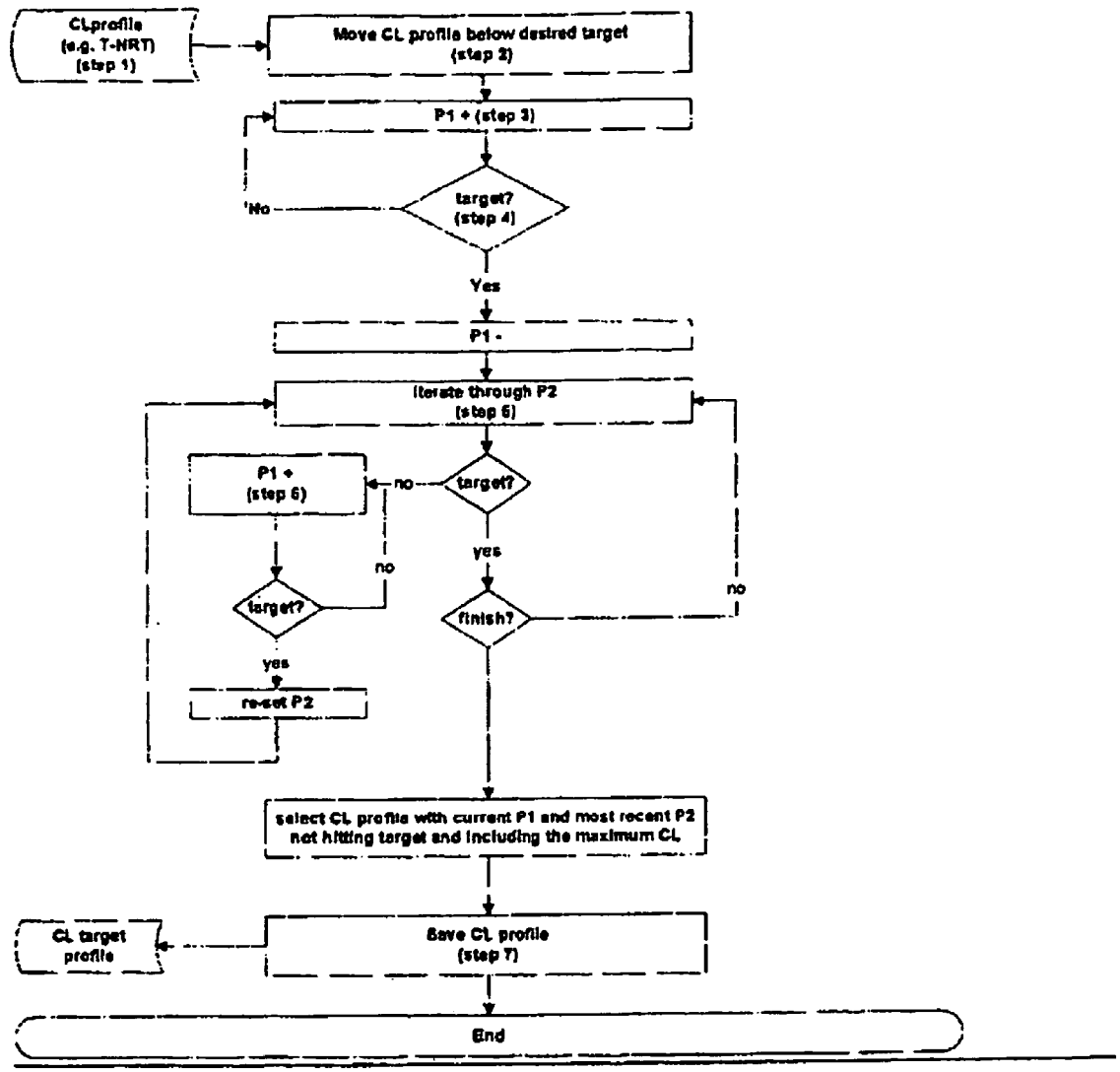
FIG. 7 is a flow chart of the method of the present invention.

An embodiment of the method according to the present invention is depicted by the flowchart in FIG. 7. This method preferably provides a more efficient method of establishing and setting the T and C levels which are specific to each particular recipient.

The method of the present invention consists essentially of 2 steps which are used in the same manner to establish the T and C levels for a recipient. The starting point in all cases is to establish an initial current level profile across all electrode channels that can be manipulated by adjusting a few profile parameters to establish the
  and C levels for that recipient. These parameters include, but are not limited to, vertical position shift, profile tilt and profile curvature of the current level profile.

The first step essentially moves each initial current level in the profile a series of increments until a target is met. This target would be either the fact that the threshold point has been determined, or that the maximum current level has been determined. Once this has occurred, the next step is to identify optimal values for other parameters describing the profile, to best achieve the target, namely that the threshold point has been achieved or that the maximum comfort point has been achieved.

The first step of the present invention is to establish a predefined initial current level (CL) profile (ie. step 1 of the flow chart). This profile gives a current level setting for each electrode channel and is the basis from which the final T and C level profiles are established. It is envisaged that more than one initial profile could be used, for example, one profile for setting T levels, another for setting C levels etc. As mentioned previously, this initial CL profile may be the result of measurements of the ECAP thresholds for each or a few of the electrodes, the result of a statistical analysis of recipient mapping data over a number of subjects, or the result of a number of electrophysiological and/or psychophysics measurements in combination with statistical analysis, such as multiple regression. It is also conceivable that the initial CL profile may be a straight line. Ideally, the initial CL profile is established without the need for subjective feedback from the recipient and without the need for multiple tests to be performed on the recipient for each specific electrode channel.

Figure 8:
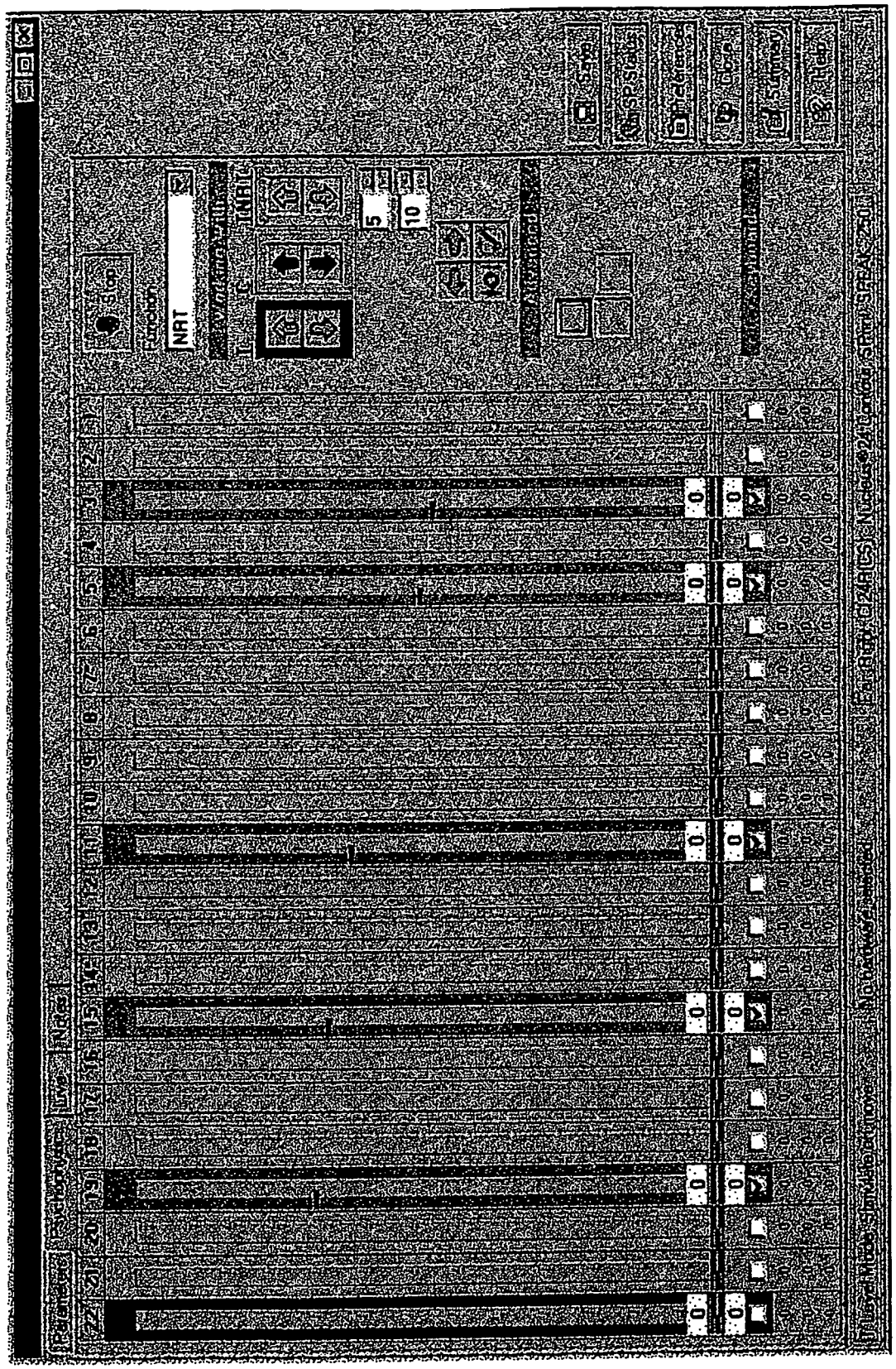
FIG. 8 shows the step of importing ECAP thresholds according to one embodiment of the present invention.
Figure 9:
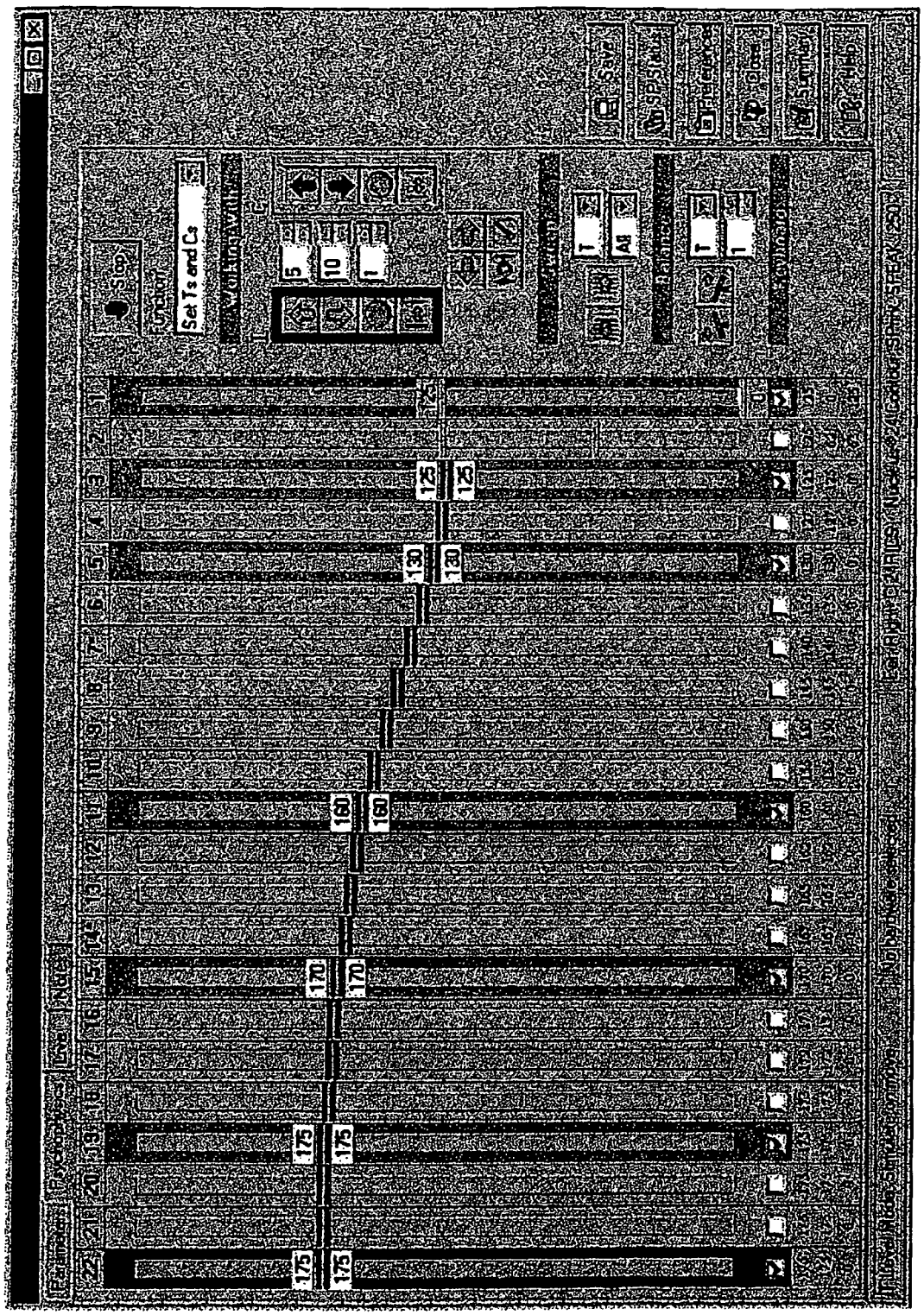
FIG. 9 shows the step of interpolating the CL profile from the imported ECAP thresholds of FIG. 8, according to an embodiment of the present invention.

As is shown in FIG. 8, the initial CL profile may be derived from a small number of measured ECAP thresholds for specific electrode channels, with the full profile being predicted for non-measured channels, similar to as is shown in FIG. 9. In this depicted example, ECAP thresholds were measured for 7 electrode channels with the values for the non-measured channels being extrapolated therefrom.

Figure 10:
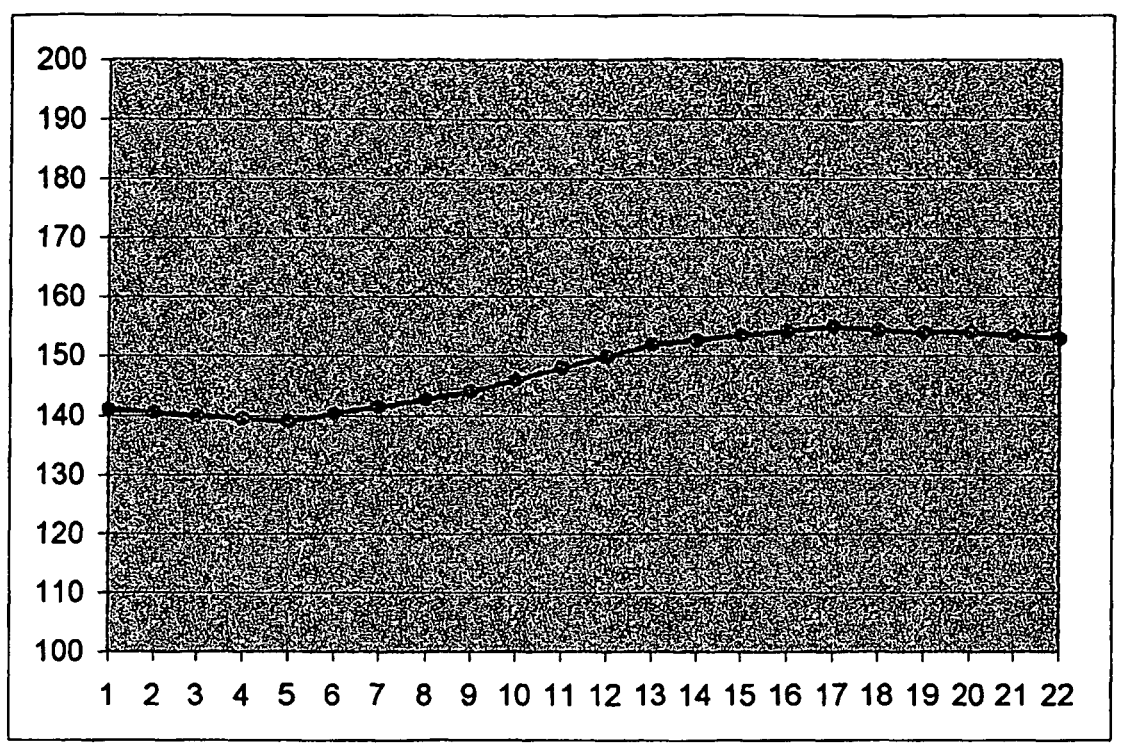
FIG. 10 shows complete ECAP thresholds used as an initial CL profile according to another embodiment of the present invention.

However, in a another embodiment, the ECAP thresholds for each channel would be used as the initial CL profile, as is shown in FIG. 10.

Once the initial CL profile has been established in step 1, it is then preferably manipulated to establish appropriate T and C levels for the recipient. In step 2 of this process, the initial profile is shifted below the predicted desired target setting. In the case of setting the T-level profile, the initial CL profile would be shifted down to a level that would be below a recipient's threshold of hearing; for example, the maximum current level of the CL profile could be reduced to a current level of 80 with all other levels being relative to this.

Figure 11:
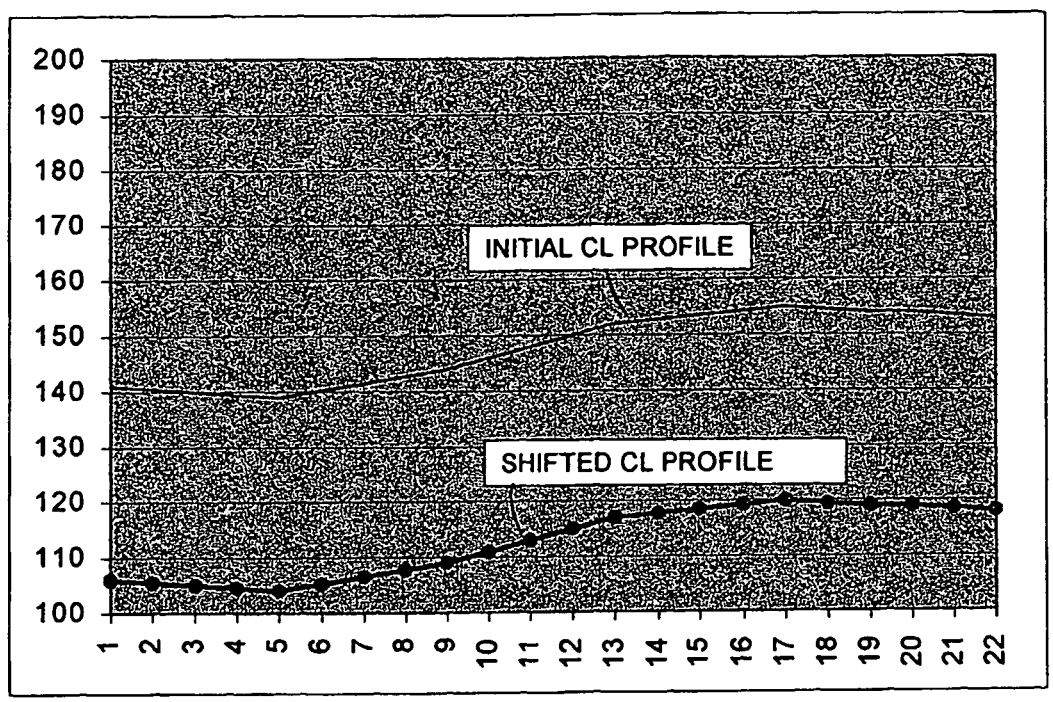
FIG. 11 shows the initial CL profile being shifted below the recipient's hearing threshold according to step 2 of FIG. 7.

In the case of setting the C level profile, the initial CL profile could be moved to any level that is below the maximum comfort level of the recipient as a starting point, for example, the previously identified threshold. A graphical example of this in relation to the setting of T levels can be seen in FIG. 11, wherein the initial CL profile is shown as the thin line, and the dotted line represents the initial CL profile being shifted down below an arbitrary threshold level, ie. should the electrodes be stimulated to those current levels, the recipient would not experience sound sensation. It is this "shift" action that provides the first manipulation or adjustment of the CL profile.

Figure 12:
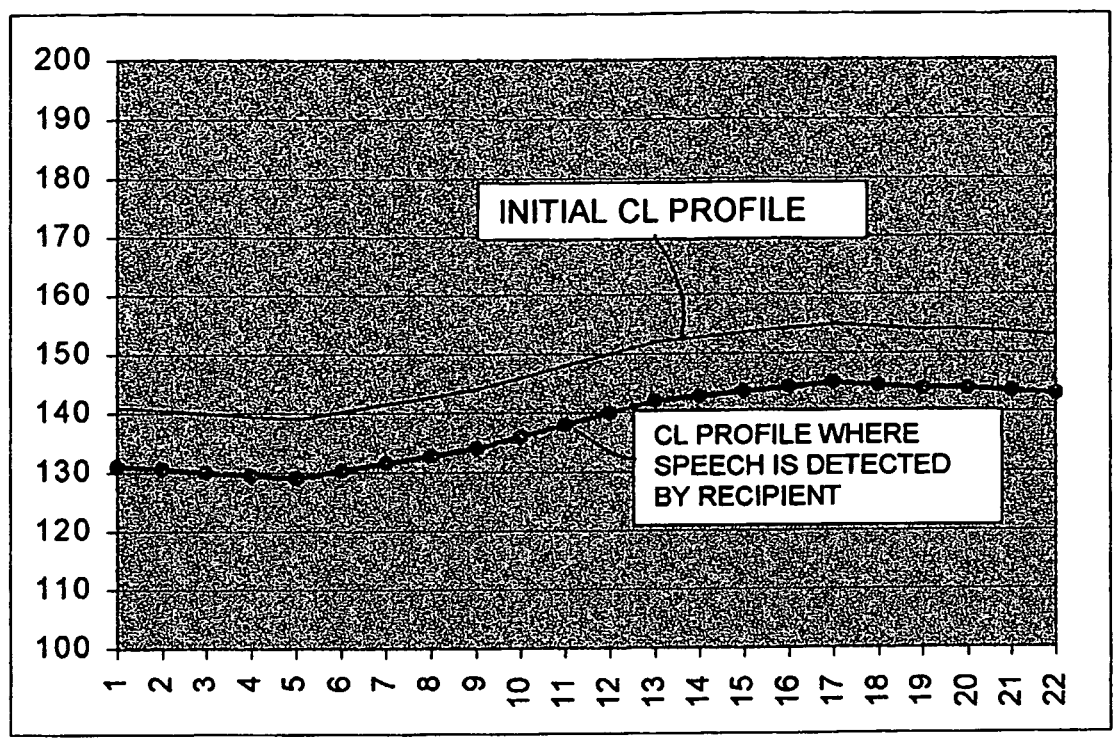
FIG. 12 shows the CL profile representative of when a recipient can just hear live speech according to steps 3 and 4 of FIG. 7.

In step 3, the recipient is presented with a broad band signal, for example a live speech sample, and the stimulation representative of this signal is delivered by the electrode array of the implant to the recipient within the constraints of the CL profile set by step 2. If the recipient does not detect the live speech, the CL profile is then shifted up or increased by a level step size (for example iterations of 5 current levels at a time) until the live speech is detected by the recipient, and what is considered as the "shift target" is met. FIG. 12 is a graphical representation of this, showing the CL profile which has been shifted up a number of level steps from that shown in FIG. 11, with this profile indicative of the point where the recipient indicates that they are detecting live speech.

At this stage in the process, the CL profile can be lowered one incremental step, and the profile manipulated by adjusting one parameter of a limited set of parameters, thereby changing the characteristics of the CL profile (ie step 5 in FIG. 7). In one embodiment, this manipulation is performed by applying a "tilt" manipulation to the profile, wherein a derived amount of current level is added/subtracted to each individual current level value for the individual electrode channels of the electrode array. This manipulation literally "tilts" the profile as represented on a graph of current level against electrode channel number. That is, the profile is shifted down for high frequency channels and up for low frequency channels or vice versa. It is envisaged that the "tilt" may be linear or non-linear, e.g. derived from a tilt profile. A software package can automatically apply this "tilt" manipulation, by using, for example, electrode channel 12 as the pivot point. In the case of a linear tilt, for each channel from 22-13, the current level is increased by a varying percentage of fixed current levels, and for each channel from 11-1, the current levels are decreased by a varying percentage of fixed current levels, or vice versa. The use of other electrode channels in the array as "pivot points" for the tilt manipulation can be envisaged.

Figure 13:
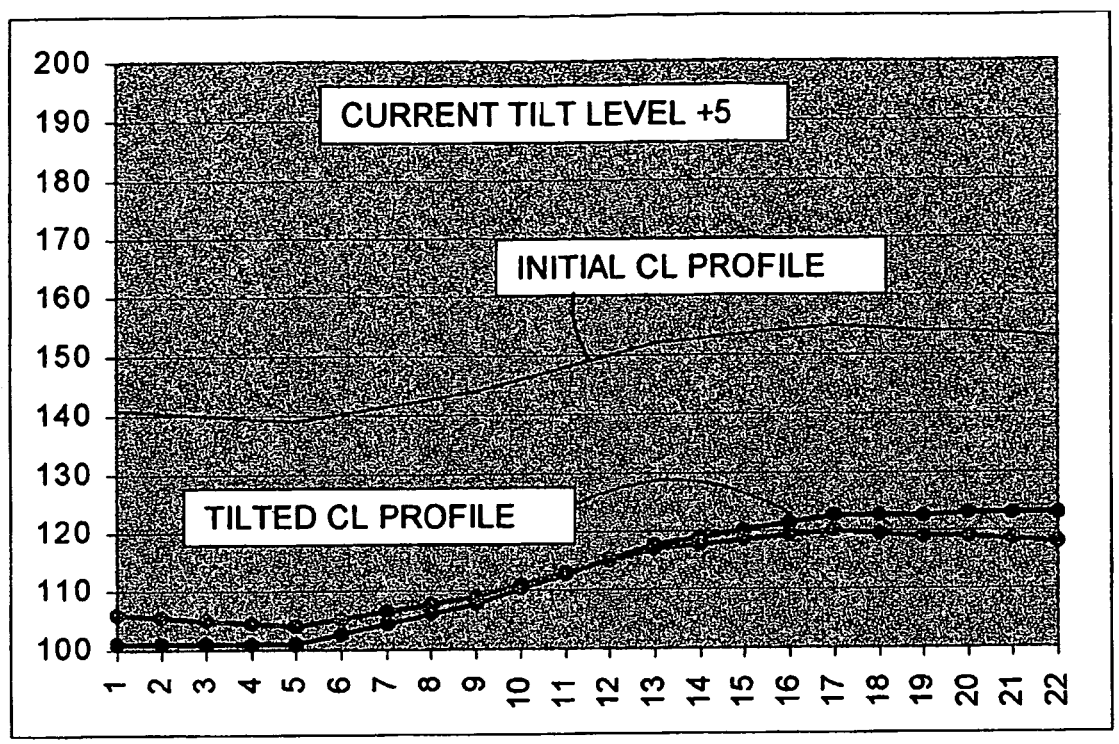
FIG. 13 shows the CL profile tilted a current level value of +5 according to step 5 of FIG. 7.
Figure 14:
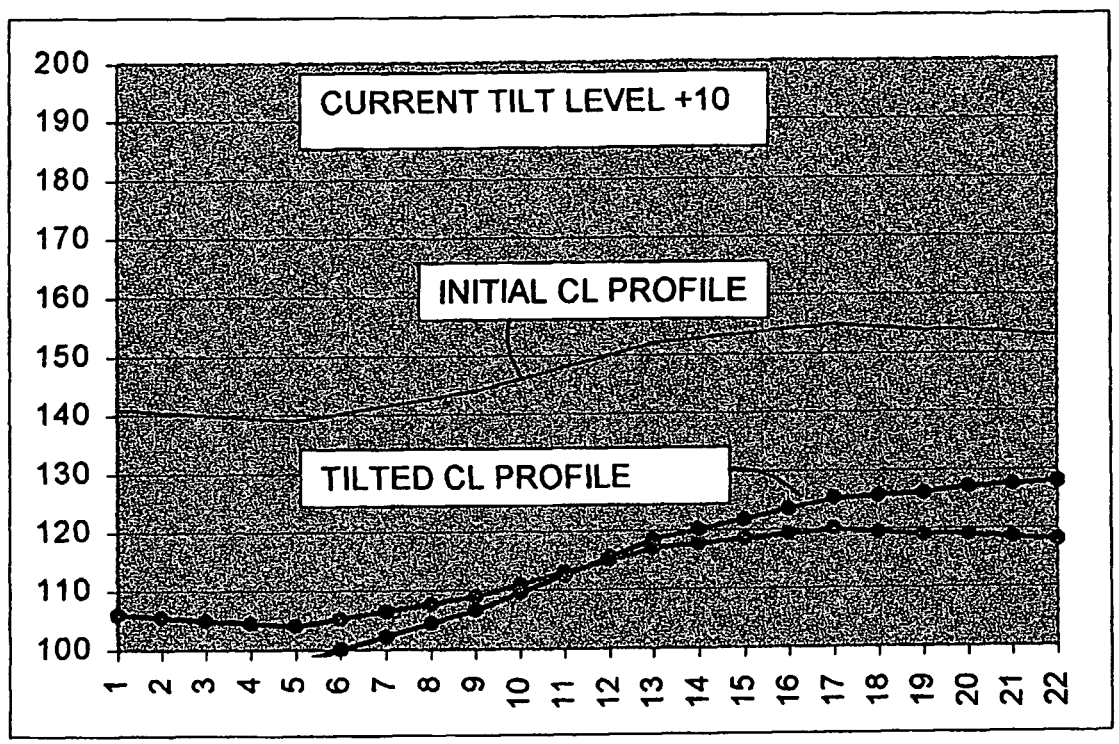
FIG. 14 shows the CL profile tilted a current level value of +10 according to step 5 of FIG. 7.
Figure 15:
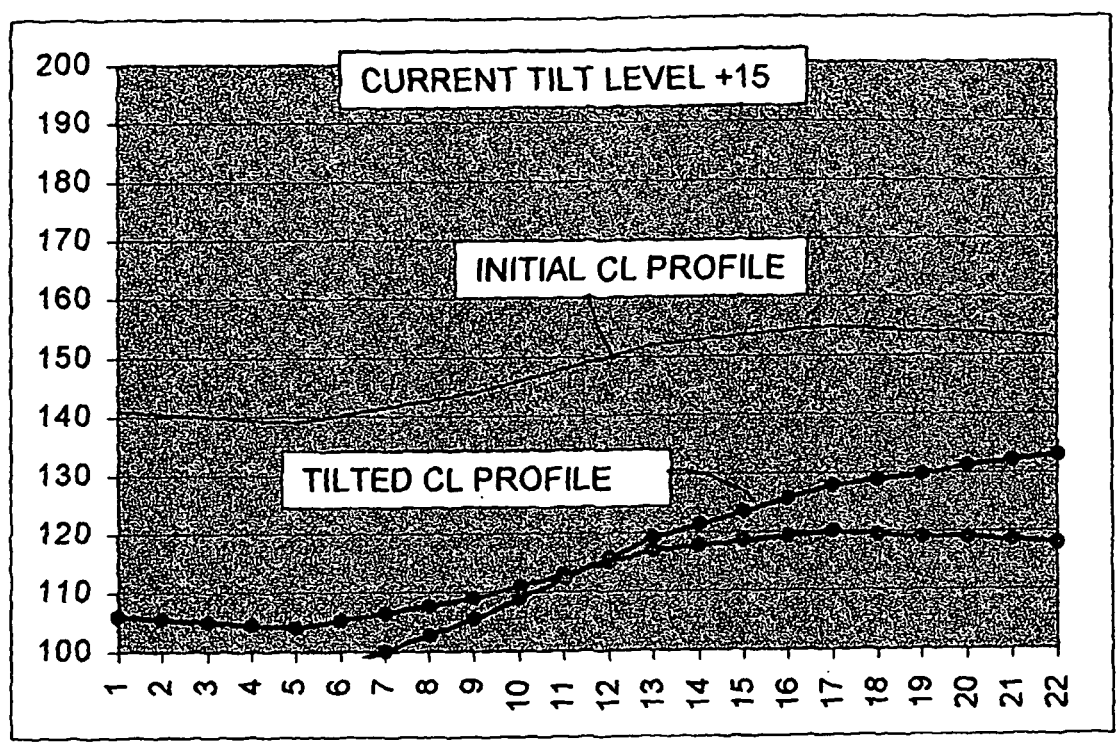
FIG. 15 shows the CL profile tilted a current level value of +15 according to step 5 of FIG. 7.
Figure 16:
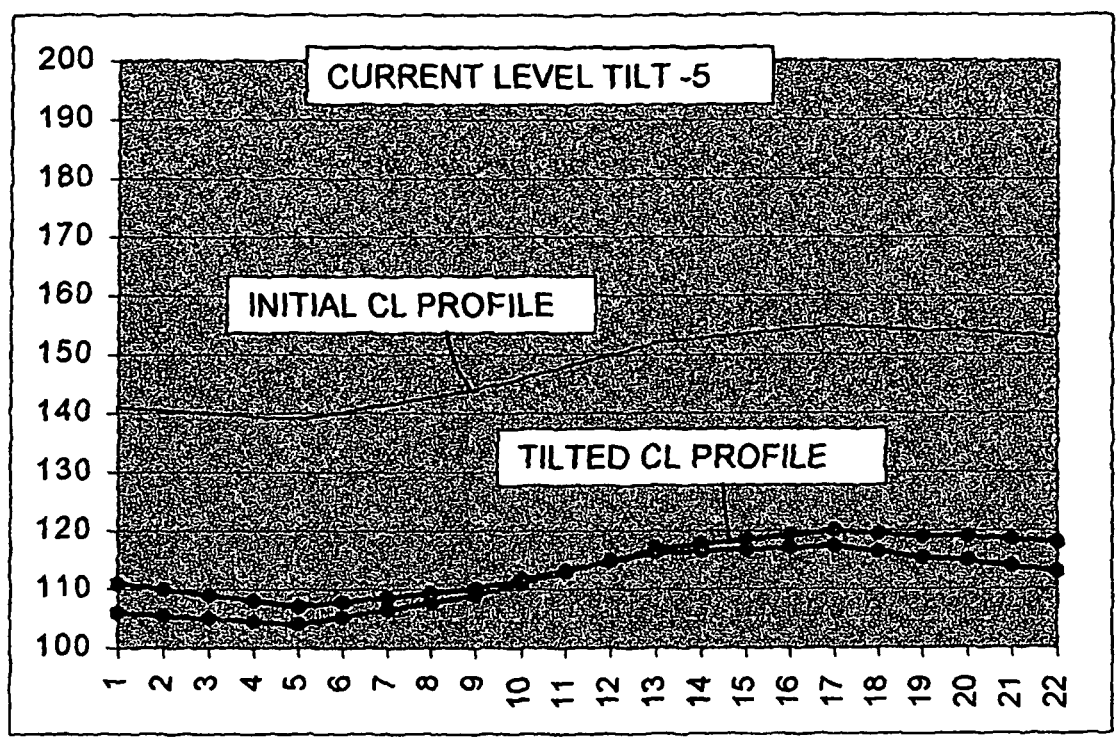
FIG. 16 shows the CL profile tilted a current level value of −5 according to step 5 of FIG. 7.
Figure 17:
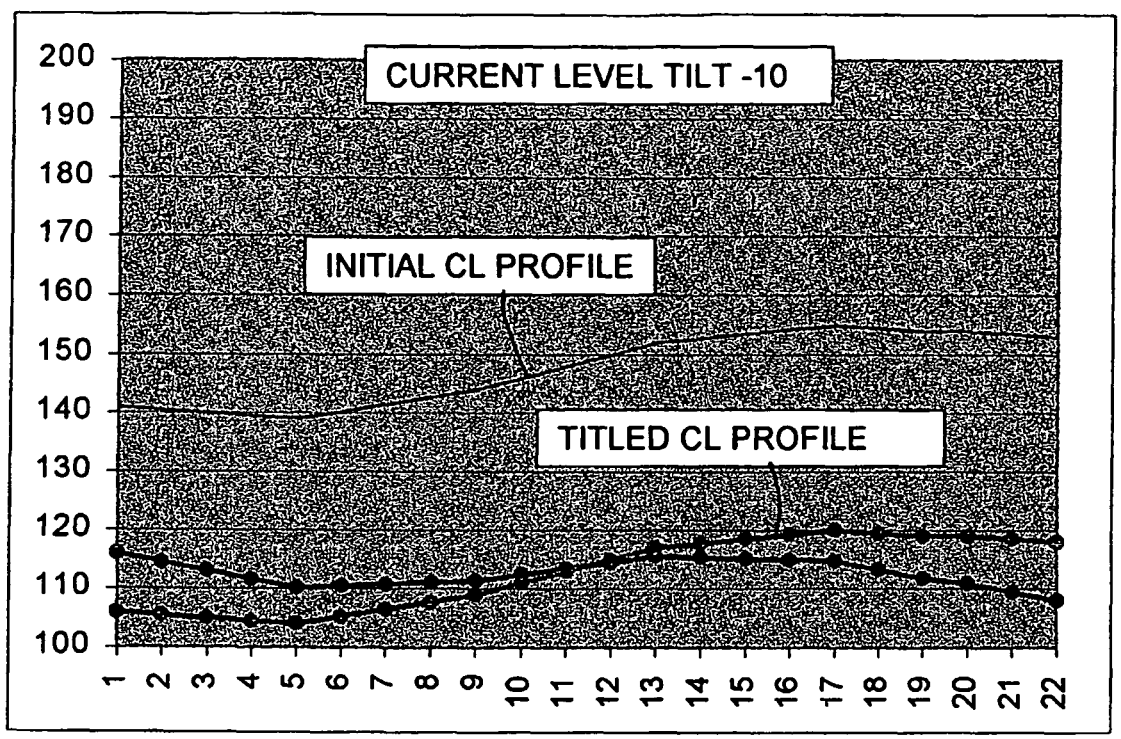
FIG. 17 shows the CL profile tilted a current level value of −10 according to step 5 of FIG. 7.

In a preferred embodiment, the fixed current level may be 5. FIG. 13 is a graphical example of such a CL profile manipulation indicative of a current level tilt of 5.

In this step of the process, the CL profile is manipulated by using the "tilt" value, until the live speech is no longer detected, ie. the target is not met. Then, step 3 as described above is repeated (shown in FIG. 7 as step 6) until the recipient can again detect the live speech.

If no further shift/tilt combination meets the target criteria (i.e. sound detection in this example), then the current value for shift is the target shift value. The target shift value is that, which did not meet the target criterion and includes the highest CL amongst the profiles using the target shift and a tilt meeting the target. This CL profile is then saved in step 7.

Figure 18:
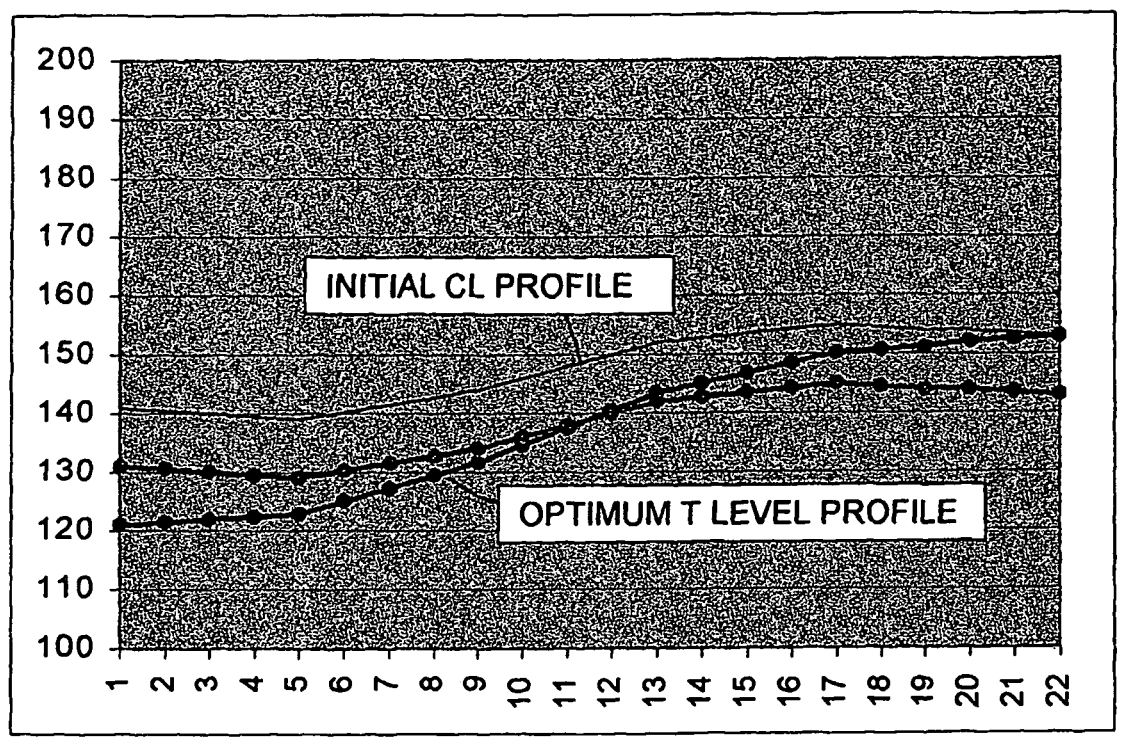
FIG. 18 shows an example of an optimum T-level profile generated from the initial CL profile according to step 9 of FIG. 7.

FIGS. 14-17 illustrate examples of different tilt values which may be used for steps 5 and 6, namely a fixed current level tilt of 10, 15, −5 or −10 may be used for these steps. FIG. 18 represents a graphical example of an optimum threshold CL level achieved using this process, ie the initial CL profile which has been shifted down 10 current levels and tilted 10 current levels.

Having met the condition leading to step 7, the optimum CL profile is set as the T-level profile for use in the recipient's map. Alternatively, the process could be continued by manipulating other profile parameters, such as profile curvature.

Whilst this process has been shown only in relation to setting the T levels, it can easily be used to set the C levels, with the only change required being the criterion of the "target". For setting the C levels, the "target" criterion is maximum comfort of sound perceived by the recipient, rather than sound detection, as is the case in setting the T levels.

Further, whilst the process described above has combined the shift and tilt functions, the two functions can be applied separately. In this regard, the shift function can be used to move the CL profile to a threshold or maximum comfort position where the tilt or other such functions can be applied to the CL profile to optimise and fine time the CL profile.

One example of the present invention being employed to set the T and C levels for an implant recipient that previously had the T and C levels set individually for each channel is described as follows:

1. An initial current level profile was set for the recipient based upon previous statistical threshold level data.

2. The initial current level profile was dropped below the recipient's threshold level.

3. The current level profile was then raised in incremental shifts in the presence of live voice until indication was obtained of the sound becoming audible to the recipient.

4. Upon establishing the point where the live signal became audible, the current level profile was fixed as the T-level profile.

5. The current level profile was then raised in incremental shifts in the presence of live voice until indication was given by the recipient of the loudness of the sound being at its maximum comfortable level.

6. The tilt of the current level profile at maximum comfort level was then increased/decreased and subjective judgement was obtained to determine the optimum current level profile which was then set as the C-level profile.

7. Step 6 was then repeated for the T-level profile.

This procedure took less than 5 minutes to complete, and the T and C levels were then programmed into their speech processor map for subsequent use. The recipient reported that sound perception using the map created by the present invention was substantially the same as the sound perception using the map created by the conventional mapping techniques.

The present invention therefore requires minimal psychophysics measurements using live voice, compared to many psychophysical measurements (roughly equivalent to twice the number of channels) using artificial stimuli as is the case in conventional mapping procedures. As a result, the present invention provides a programming/mapping procedure that is more recipient friendly, and makes the fitting procedure, especially for small children, simpler, more time efficient and more cost effective then has historically been the case.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of fitting an auditory stimulation system having a plurality of channels to a recipient, the method comprising:
   establishing a first current level profile comprising a first current level setting for each of the plurality of channels;
   applying stimulation using the first current level profile;
   obtaining a response to the applied stimulation;
   based on the obtained response, adjusting more than one of the first current level settings to effectuate a tilt of the first current level profile about a pivot point on the first current level profile and thereby generate a second current level profile; and
   applying stimulation using the second current level profile.

2. An apparatus configured to interface with an auditory stimulation system having a plurality of channels, wherein the apparatus is further configured to establish a first current level profile comprising a first current level setting for each of the plurality of channels; display a graphical representation of the first current level profile; instruct the auditory stimulation system to apply stimulation using the first current level profile; obtain a response to the applied stimulation; adjust, based on the obtained response, more than one of the first current level settings to effectuate a tilt of the first current level profile about a pivot point on the profile and thereby generate a second current level profile; and provide the second current level profile to the auditory stimulation system for use in applying stimulation using the second current level profile.

3. The apparatus of claim 2, wherein to establish the first current level profile the apparatus is configured to measure evoked compound action potential (ECAP) thresholds for at least one channel of the auditory stimulation system; and interpolate the first current level profile from the measurements.

4. The apparatus of claim 2, wherein to establish the first current level profile, the apparatus is configured to use a statistical analysis of recipient mapping data over a number of recipients in establishing the first current level profile for a particular recipient.

5. The method of claim 2, wherein to establish the first current level profile for the particular recipient, the apparatus is configured to perform psychophysical measurements of the particular recipient in combination with a statistical analysis of recipient mapping data over a number of recipients, to thereby determine the first current level profile for the particular recipient.

6. The apparatus of claim 2, wherein to effectuate the tilt, the apparatus is configured to increase or decrease each of the more than one of the first current level settings by a derived amount.

7. The apparatus of claim 6, wherein to effectuate the tilt, the apparatus is configured to adjust the current level settings of channels located on one side of the pivot point in a particular direction and adjust the current level setting in the opposite direction for channels located on the other side of the pivot point.

8. The apparatus of claim 7, wherein the auditory stimulation system is configured to be implanted in a cochlea and comprises a plurality of electrodes for applying stimulation to the cochlea, wherein to effectuate the tilt, the apparatus is configured to increase the first current level setting for channels corresponding to electrodes positioned in the apical region of the cochlea and decrease the first current level setting for channels corresponding to electrodes positioned in the basal region of the cochlea.

9. The apparatus of claim 7, wherein the auditory stimulation system is configured to be implanted in a cochlea and comprises a plurality of electrodes for applying stimulation to the cochlea, wherein to effectuate the tilt, the apparatus is configured to decrease the first current level setting for channels corresponding to electrodes positioned in the apical region of the cochlea and increase the first current level setting for channels corresponding to electrodes positioned in the basal region of the cochlea.

10. The apparatus of claim 2, wherein the applied stimulation is derived from a broadband sound signal.

11. The apparatus of claim 10, wherein the broadband sound signal is a live speech signal.

12. The apparatus of claim 10, wherein the broadband sound signal is an artificial signal.

13. The apparatus of claim 10, wherein the broadband sound signal is a recorded signal.

14. The method of claim 1, wherein the tilt is a linear tilt.

15. The method of claim 1, wherein the tilt is a non-linear tilt.

16. The method of claim 1, wherein the second current level profile is representative of a recipient's threshold or maximum comfort current level profile.

17. The method of claim 1, wherein establishing the first current level profile comprises:
measuring evoked compound action potential (ECAP) thresholds for at least one channel of the auditory stimulation system; and
interpolating the first current level profile from the measurements.

18. The method of claim 1, wherein establishing the first current level profile comprises:
performing a statistical analysis of recipient mapping data over a number of recipients and subsequently using the analysis in establishing the first current level profile for a particular recipient.

19. The method of claim 1, wherein establishing the first current level profile comprises:
performing psychophysical measurements of a particular recipient in combination with statistical analysis of recipient mapping data over a number of recipients to thereby determine a suitable first current level profile for the particular recipient.

20. The method of claim 1, wherein the tilt is effectuated by increasing or decreasing each of the more than one of the first current level settings by a derived amount of current.

21. The method of claim 20, wherein to effectuate the tilt, the method comprises:
adjusting the current level settings of channels located on one side of the pivot point in a particular direction; and
adjusting the current level setting in the opposite direction for channels located on the other side of the pivot point.

22. The method of claim 21, wherein adjusting the more than one of the first current level settings comprises:
before adjusting the more than one of the first level settings, positioning, in a cochlea of a recipient, an electrode array comprising a plurality of electrodes for applying stimulation for the channels; and
increasing the first current level setting for channels corresponding to electrodes positioned in the apical region of the cochlea and decreasing the first current level setting for channels corresponding to electrodes positioned in the basal region of the cochlea.

23. The method of claim 21, wherein adjusting the more than one of the first current level settings comprises:
before adjusting the more than one of the first level settings, positioning, in a cochlea of a recipient, an electrode array comprising a plurality of electrodes for applying stimulation for the channels; and
decreasing the first current level setting for channels corresponding to electrodes positioned in the apical region of the cochlea and increasing the first current level setting for channels corresponding to electrodes positioned in the basal region of the cochlea.

24. The method of claim 1, wherein the applied stimulation is derived from a broadband sound signal.

25. The method of claim 24, wherein the broadband sound signal is a live speech signal.

26. The method of claim 24, wherein the broadband sound signal is an artificial signal.

27. The method of claim 24, wherein the broadband sound signal is a recorded signal.

28. The method of claim 1, further comprising:
establishing an initial current level profile comprising an initial current level setting for each of the plurality of channels;
wherein establishing the first current level profile comprises:
increasing each initial current level setting by a fixed amount until the stimulation signal can just be detected by the recipient, indicative of the stimulation reaching a threshold level.

29. The method of claim 28, wherein the second current level profile comprises a second current level setting for each of the channels, the method further comprising:
increasing at least one of the second current level settings and decreasing at least one of the second current level settings to determine an optimum T-level profile.

30. A method of fitting an auditory stimulation system, having a plurality of channels, to a recipient, the method comprising:
establishing a first current level profile comprising a current level setting for each of the plurality of channels, wherein establishing the first current level profile comprises:

measuring a first threshold for each channel of a first subset of the plurality of channels, wherein the first subset comprises fewer than all of the channels; and determining, from the measured first thresholds, the current level setting for each channel of the plurality of channels;

applying stimulation using the first current level profile;

obtaining a response to the applied stimulation; and adjusting a plurality of the current level settings by effectuating a tilt of at least a portion of the first current level profile about a pivot point on the at least a portion of the first current level profile based on the obtained response.

31. The method of claim 30, wherein the measured first thresholds are evoked compound action potential (ECAP) thresholds.

32. The method of claim 30, wherein the measured first thresholds are set as the current level settings for the channels of the first subset.

33. The method of claim 30, wherein determining from the measured first thresholds the current level setting for each channel of the plurality of channels comprises:

extrapolating from the measured first thresholds the current level settings for each channel of a second subset of the plurality of channels.

34. An apparatus configured to interface with an auditory stimulation system having a plurality of channels, the apparatus comprising:

means for establishing a first current level profile comprising a first current level setting for each of the plurality of channels;

a graphical display means configured to display a graphical representation of the first current level profile;

means for instructing the auditory stimulation system to apply stimulation using the first current level profile;

means for obtaining a response to the applied stimulation;

mean for adjusting, based on the obtained response, more than one of the first current level settings to effectuate a tilt of the first current level profile about a pivot point on the profile and thereby generate a second current level profile; and means for providing the second current level profile to the auditory stimulation system for use in applying stimulation using the second current level profile.

* * * * *